United States Patent [19]

Groch et al.

[11] Patent Number: 4,546,777
[45] Date of Patent: Oct. 15, 1985

[54] HEART SOUND DETECTOR AND SYNCHRONIZATION FOR DIAGNOSTICS

[75] Inventors: Mark W. Groch, Elk Grove; James R. Domnanovich, Roselle, both of Ill.

[73] Assignee: Siemens Gammasonics, Inc., Des Plaines, Ill.

[21] Appl. No.: 583,083

[22] Filed: Feb. 23, 1984

Related U.S. Application Data

[62] Division of Ser. No. 241,388, Mar. 6, 1981, Pat. No. 4,496,873.

[51] Int. Cl.[4] ............................................. A61B 5/02
[52] U.S. Cl. .................................................. 128/715
[58] Field of Search ............. 128/689, 695, 696, 700, 128/702–704, 706, 710, 715

[56] References Cited

U.S. PATENT DOCUMENTS

| 3,030,946 | 4/1962 | Richards | 128/715 |
| 3,280,317 | 10/1966 | Jorgensen et al. | 128/700 |
| 4,248,244 | 2/1981 | Charnitski | 128/706 |
| 4,250,888 | 2/1981 | Grosskopf | 128/702 |

*Primary Examiner*—William E. Kamm
*Attorney, Agent, or Firm*—John Francis Moran

[57] ABSTRACT

From a heart sound signal input the occurrence of a first occurring heart sound is detected. Thereupon a predetermined heart sound enable window time is established, which for a first detection cycle is set to approximately the diastolic interval for the maximum heart rate to be detected. If a second heart sound occurs within this heart sound enable window time, this second heart sound is detected as a systole heart sound. The first heart sound may be detected as a diastole heart sound. If a second heart sound does not occur within the heart sound enable window time the procedure is repeated with increasing heart sound enable time as long as a second heart sound occurs within an increased heart sound enable window time. For diagnostics synchronization signals developed exclusively from the heart sound signals are used to validate data from diagnostic equipment such as a gamma camera.

15 Claims, 18 Drawing Figures

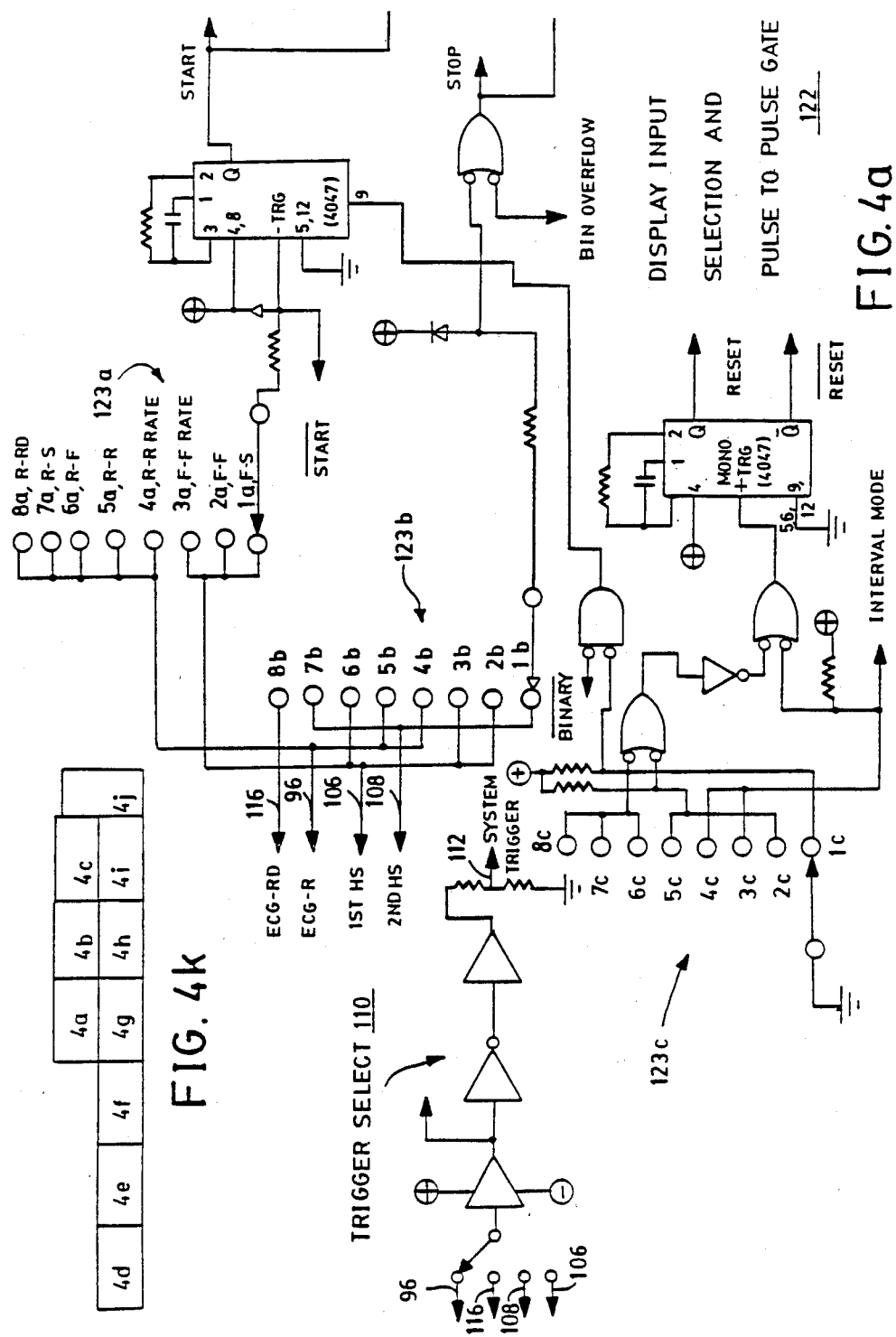

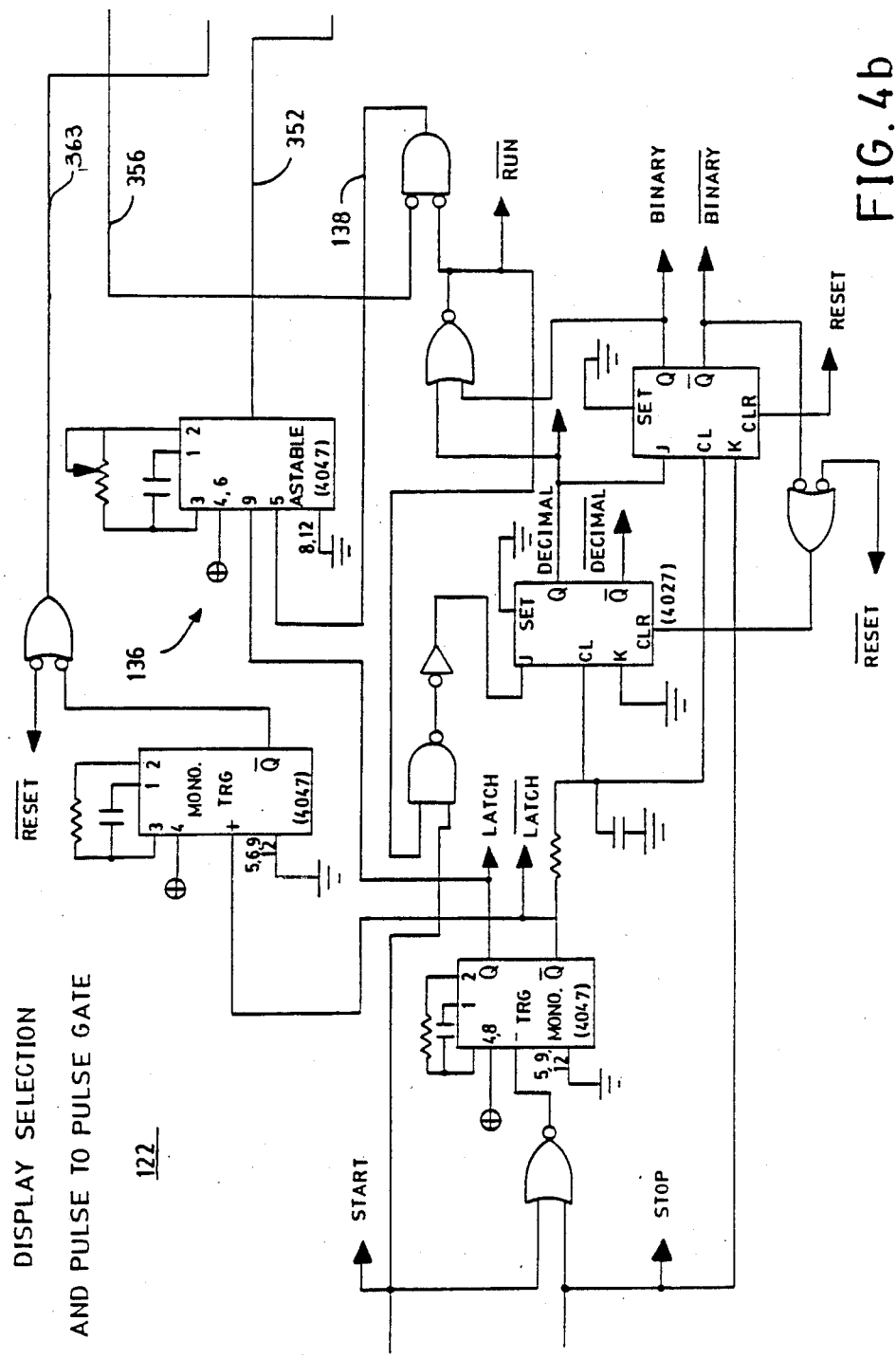

HEART SOUND DETECTOR AND SYNCHRONIZATION FOR DIAGNOSTICS

REFERENCE TO A RELATED APPLICATION

This application is a divisional of application Ser. No. 241,388, filed Mar. 6, 1981 now matured into U.S. Pat. No. 4,496,873 issued May 8, 1984.

BACKGROUND OF THE INVENTION

A. Field of the Invention

The present invention relates generally to the medical diagnostic field and more particularly to a method and apparatus for detecting heart sounds and for generating accurately timed reference signals coincident with the first and second heart sounds of a cardiac cycle. The present invention further relates to the control of medical diagnostic imaging apparatus based on first and/or second heart sound reference signals.

B. Description of the Prior Art

Various medical diagnostic methods and apparatus of the prior art have attempted to detect heart sounds and to distinguish between the first and second heart sounds by amplitude or by gating with the R wave of the ECG. Further, the prior art arrangements utilize the timing relationships between successive heart sounds and the first and second heart sounds for analysis purposes. Other prior art arrangements have attempted to synchronize, gate or trigger cardiac imaging apparatus on the basis of heart sound amplitudes, patient cardiac pulse signals, or electrocardiogram signals and delay techniques.

For example, U.S. Pat. No. 4,094,308 to Cormier detects heart sounds to develop an electrical phonocardiogram via an inverse filter network denoted as a deconvolution function. A phonocardiogram transducer is placed in contact with the chest of a patient whereupon acoustical energy of the heart sounds is converted into electrical energy. The resultant signal waveform after the deconvolution filter provides impulse functions for each heart sound with the basic purpose of the apparatus to determine the systolic time intervals such as: (1) the pre-ejection phase or period denoted as the elapsed time from the Q-wave onset (in the electrocardiogram waveform) to the opening of the aortic valve; or (2) the left ventricular ejection time equal to the length of time the aortic valve remains open as determined by the time difference between the two impulse signals. The apparatus distinguishes the impulses derived from the heart sounds on the basis of amplitude to establish timing markers for the measurement of the systolic time intervals and the accompanying heart rate. The larger amplitude signal is stated to occur during the closing of the aortic valve. Pulse height detection of the rectified signals resulting from the process is achieved with hysteretic comparators and with digital level converters regulating extracted voltages and current pulses to trigger digital logic networks and microcomputer circuits which selectively activate electronic counters, timers and dividers to measure the pre-ejection phase, the left ventricular ejection time, the ratio of these two quantities, and the heart rate.

U.S. Pat. No. 3,318,303 to Hammacher measures heart sounds by use of a contact microphone and provides outputs distinguishing the first and second heart sounds of each heart cycle by generating impulses coincident with each heart sound. While the first and second heart sounds are distinguished and separately analyzed, the first and second heart sounds are not differentiated by the timing relationships between the heart sounds in the overall heart cycle but merely by the state of a flip-flop which changes state upon the detection of each heart sound to thereby output two series of pulses, one for each heart sound in each heart cycle. The purpose of the Hammacher method and apparatus is to accurately determine heart beat frequency by comparing the periodic rates of each of the pulse trains corresponding to the first and second heart sounds and comparing the heartbeat frequency rate between the two pulse trains. Hammacher also mentions the detection of the first heartbeat by combination with the R-wave of the ECG.

U.S. Pat. No. 3,581,735 to Gentner, et al. is directed to phonocardiographic apparatus for measuring fetal heart frequency and utilizes the relationships of detected heart sounds in accordance with the overall period of the heart rate to detect missed heartbeats to provide accurate indications of the heart frequency. Specifically, the analysis utilizes physiological criteria to determine if heart sounds have been missed by comparing the time between successive detected heart sounds and the overall heart cycle to determine if an accurate heart frequency has been detected. For example, if the second heart sound is not detected and missed, a low heart rate frequency results and the ratio between successive heart sounds and the overall period is analyzed and if this ratio is approximately equal, it is determined that a heart sound has been missed; since at low heart rate frequencies such a ratio is physiologically impossible as the time between the first and second heart sounds is much less than the time between the second heart sound of the first cycle and the first heart sound of the next cycle for low frequency heart rates. However, if a high heart rate frequency is detected and the ratio is approximately equal, it is determined that an accurate heart rate frequency has been detected. There is no distinguishing between the first and second heart sounds as the systolic and diastolic events to differentiate the heart sounds.

U.S. Pat. No. 3,498,292 to Jorgensen, et al. is directed to a heart sound sequence indicator to detect and indicate the first and second heart sounds and their respective intervals on respective systolic and diastolic indicators. The determination and distinguishing of the heart sounds is achieved by derivation from the electrocardiogram waveform and appropriate timing circuitry and the arrangement does not directly detect or discriminate heart sounds.

U.S. Pat. Nos. 3,954,098, 3,171,892, 3,921,623, U.S. Pat. No. Re. 27,042, U.S. Pat. Nos. 3,878,832 and 3,132,208 are directed to various prior art techniques that analyze heart sounds for various purposes. For example, U.S. Pat. No. 3,171,982 utilizes an acoustic pickup device for detection of the fetal heart rate within another organism and utilizes pulse duration discriminator means to distinguish the fetal heart rate pulse waves from that of the mother by the pulse width of the heartbeat rate signals. U.S. Pat. No. 3,954,098 to Dick et al is directed to heart display apparatus and triggering of the display from a delayed ECG signal. U.S. Pat. No. 3,921,623 is directed to an acoustical heartbeat measuring circuit for analyzing specific frequencies occurring in the heartbeat and includes a filter having a predetermined frequency response to output an indication of a number of output signals. U.S. Pat. No. Re. 27,042 is directed to an examination of the characteristics of heart sounds as detected by a microphone pickup. An electrocardiogram sequencing network controls the systolic and diastolic interrogation intervals and thus the heart sounds are detected under control of the electrocardiogram sequencing. U.S. Pat. No. 3,878,832 is directed to a system for analyzing heart defects as detected by random noise from a composite signal that includes a periodic portion and a random noise portion. U.S. Pat. No. 3,132,208 is directed to a variable conductivity gate circuit for amplifier selectivity in an electronic stethoscope.

Considering various prior art techniques for utilizing heart sounds and/or ECG signals to control diagnostic display, U.S. Pat. No. 3,220,404 to DelLucchese is directed to a combined X-ray and phonocardiographic camera wherein the horizontal sweep of a display device is gated when heart sounds detected by a microphone exceed a predetermined level.

U.S. Pat. No. 2,190,389 to Strauss, et al. is directed to the control of X-ray apparatus by means of a heart movement or pulse beat pickup and providing an adjustable time delay to activate the X-ray tube of the apparatus. A pulse pickup is affected by means of a compression cuff or bag applied to the wrist with pressure variations being transmitted to act upon a piezoelectric crystal.

U.S. Pat. No. 3,825,751 to Geratsdorfer is directed to a method of activating X-ray apparatus by means of electrocardiogram signals and providing a predetermined delay to activate the apparatus for approximating the appropriate time of activation based on the electrocardiogram waveform.

U.S. Pat. No. 3,626,932 to Becker is directed to a method and apparatus for producing a double exposure, X-ray photograph of a heart at two different points during the cardiac cycle by causing an X-ray machine to produce an X-ray burst at a first given point in a cycle and then another burst at a second different point during the cycle. The method and apparatus utilizes a synchronizer for detecting the R-wave peak from electrocardiogram waveform and includes various adjustable pulse delay means for proper synchronization.

U.S. Pat. No. 3,557,371 to Becker is similarly directed to a method and apparatus for calibrating a cardiac X-ray synchronizer to cause an X-ray machine to produce an X-ray burst at a given adjustable point in the cardiac cycle of a patient disposed in the burst path. The R-wave peak in the electrocardiogram waveform is detected to produce a signal actuating the machine at a given adjustable time after the R-wave peak.

U.S. Pat. No. 2,152,045 to Gulland is directed to a body operated switch apparatus for synchronizing X-ray exposures utilizing a mercury switch mechanically operated by pulse, respiratory or other movements of the body and includes delayed action for timing exposures of X-rays or other photographs of the heart, lungs, etc.

U.S. Pat. No. 3,344,275 to Marchal, et al. is directed to radiology apparatus for effecting a simultaneous recording of a relatively slow variation of density such as of the lungs during respiration and also of the small variations of density due to the circulation of the blood. Activation of the two channels of information is controlled by an electrocardiogram input.

U.S. Pat. No. 4,240,440 to Groch et al. is directed to method and apparatus for obtaining a nuclear kymogram of regional heart wall motion in synchronism with a display of the ECG signal; and display being triggered under the control of the ECG signal.

Various other display arrangements controlled by the ECG signals are described in the following publications:

"Clinical Assessment of Left Ventricular Regional Contraction Pattern and Ejection Fraction by Height Resolution Gated Scintography", Berman et al., *Journal of Nuclear Medicine,* Volume 16, Number 10, pp. 865–874;

"Thallium-201 Myocardial Imaging: Characterization of the ECG-Synchronized Imager", Hamilton et al., *Journal of Nuclear Medicine,* Volume 19, Number 10, pp. 1103–1110;

"Left Ventricular Function in Acute Myocardial Infarction Evaluated by Gated Scintiphotograph", Rigo et al., *Circulation,* Volume 50, pp. 678–684, 1974;

"A Real-Time System for Multi-Image Gated Cardiac Studies", Bacharach et al., *Journal of Nuclear Medicine,* Volume 18, Number 1, pp. 79–84, 1977; and "Comparison of Defect Detection or Ungated vs. Gated Thallium-201 Cardiac Imager", McKusick et al., *Journal of Nuclear Medicine,* Volume 19, Number 6, p. 725.

U.S. Pat. No. 3,993,995 to Kaplan, et al. is directed to a respiration monitor and utilizes arrangements for the automatic triggering of an X-ray machine at the instance of respiration extremes.

Thus, while the arrangements of the prior art have attempted to detect and distinguish between heart sounds, these prior art arrangements are not entirely suitable for accurately distinguishing between the first and second heart sounds and for providing accurately timed reference signals synchronized with the first and/or second heart sounds. Further, the prior art arrangements do not provide accurate and efficient diagnostic analysis to synchronize analysis data and/or images by accurately timed first and/or second heart sounds.

SUMMARY OF THE INVENTION

Accordingly, it is a principal object of the present invention to provide a method and apparatus for detecting heart sounds and for generating accurately timed reference signals coincident with the first and second heart sounds of a cardiac cycle based on the time relationship of the detected heart sounds.

It is another object of the present invention to provide a method of controlling diagnostic apparatus to provide accurately synchronized data analysis and/or images of cardiac function under the control of accurate first and/or second heart sound signals.

It is a further object of the present invention to provide a method and apparatus for providing first and second heart sound signals wherein the heart sound signals are distinguished and provided only when the two sequenced signals satisfy a time relationship such that both signals occur within a window of time, the appropriate window of time being selected in accordance with the cardiac cycle of the patient being monitored and predetermined characteristics of the cardiac cycle.

It is yet another object of the present invention to provide a method of controlling cardiac diagnostic apparatus wherein an accurately determined second heart sound signal is utilized to correct the gating of analysis data or to accurately initiate analysis throughout the diastolic interval starting at systole.

It is a further object of the present invention to provide a method of controlling the accumulation of cardiac data through the use of accurate first and/or second heart sound signals for patients with pacemakers, serious arrhythmias and other cardiac characteristics that cause distortion of the electrical impulse denoted as ECG or functional relationships that cause spurious heart sounds that could be erroneously detected as the first or second heart sound.

Briefly, these and other objects of the present invention are efficiently achieved by providing a method and apparatus for detecting heart sounds and for generating accurately timed reference signals coincident with the first and second heart sounds of a cardiac cycle. The detection and generation of the first and second heart sound signals are based on the time relationship of the detected heart sounds. Further, there is provided a method of utilizing the generated first and second heart sound reference signals for synchronization or gating of medical diagnostic imaging apparatus. Thus the medical diagnostic imaging apparatus is controlled to accept data or an image as determined by the first and/or second heart sound reference points for improved diagnostic purposes. For example, the diagnostic apparatus may be controlled to provide improved diagnostic information for phase analysis of gated blood pool studies. The heart sound detecting apparatus further provides for detection based on either the timing relationship between the heart sounds or by the R-wave of the ECG signal. The heart sound detecting apparatus includes a display to selectively provide a read-out of the time interval or rate of various heart cycle parameters including first to second heart sound time interval, first heart sound to first heart sound rate or time interval, heart rate, heart cycle period, R-wave to R-wave rate or interval, R-wave to first heart sound time interval, R-wave to second heart sound time interval, and R-wave to R-delay signal as selected on the apparatus. The heart sound detecting apparatus includes arrangements for the simultaneous recording and playback of heart sounds and the ECG waveform signals on a common channel or track.

The invention both as to its organization and method of operation together with further objects and advantages thereof will best be understood by reference to the following specifications taken in conjunction with the accompanying drawings.

BRIEF DESCRIPTION OF THE DRAWING

FIGS. 4a through j when assembled as shown in FIG. 4k from a schematic, logic and block diagram representation of a detailed specific embodiment of the heart sound detection and triggering apparatus of FIG. 1.

DETAILED DESCRIPTION OF THE PREFERRED EMBODIMENT

Figure 1:
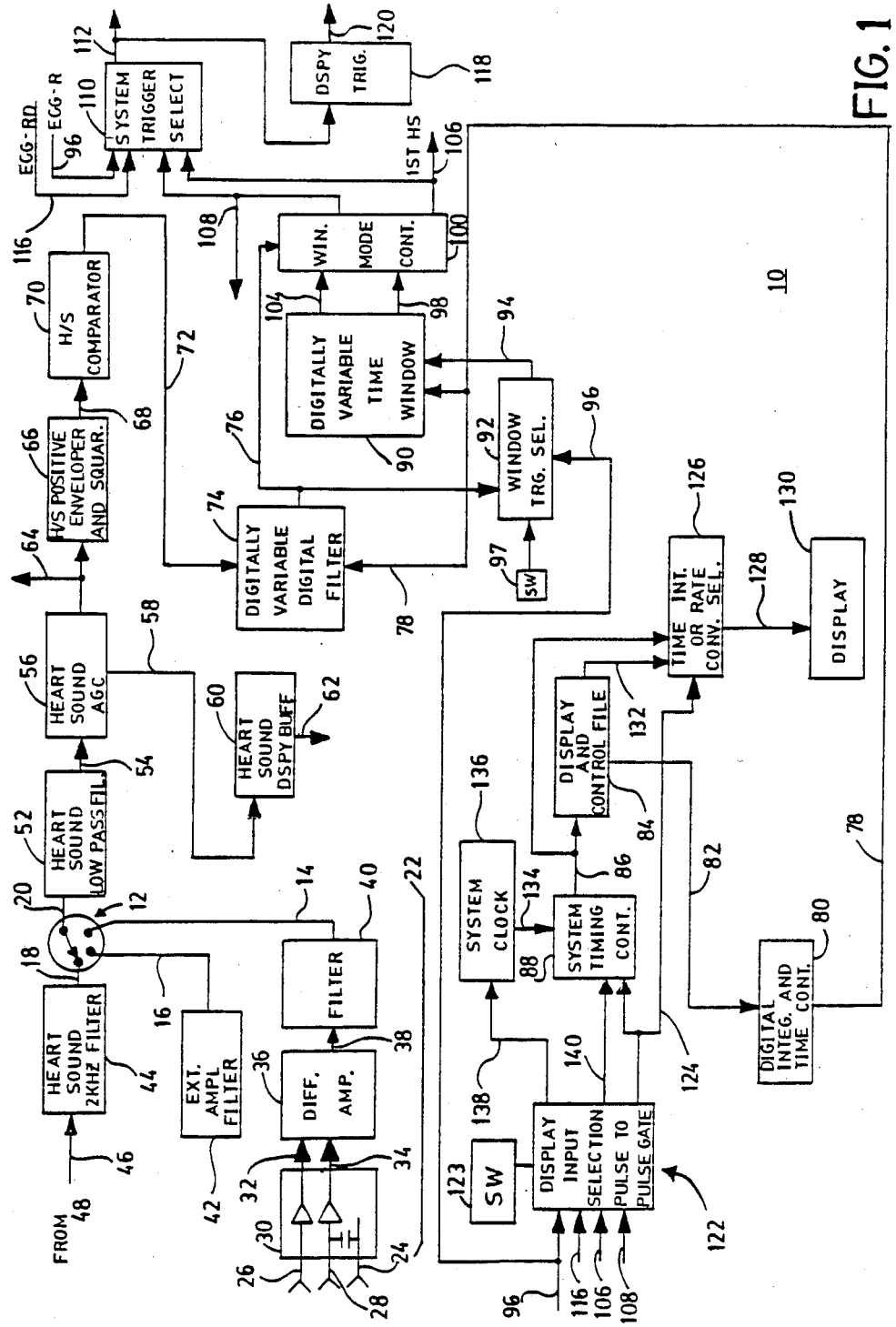
FIG. 1 is a block diagram representation of heart sound detection and gating apparatus to generate first and second heart sound signals in accordance with the present invention.

Referring now to FIG. 1, the heart sound detection and triggering apparatus 10 of the present invention includes a heart sound signal selector switch 12 that selectively connects one of three heart sound audio signal inputs 14, 16 or 18 to a common output 20 of the selector switch 12.

The heart sound signal input 14 is derived at the output of a sound transducing circuit 22 from either a single sound transducer input 24 or from dual sound transducing inputs 26, 28. The sound transducing inputs 24, 26, 28 are connected in various applications to sound transducing apparatus or microphones placed on the chest of a patient under investigation. The dual sound transducing inputs 26 and 28 are each respectively connected to a sound transducer placed on a different chest position. Accordingly, one sound transducer receives a higher amplitude from the heart sounds of a patient through the chest cavity while the second sound transducer receives a relatively lower amplitude heart signal based on the positioning of the second sound transducer at a somewhat more remote location from the heart position. Thus, the sound transducing inputs at 26 and 28 receive essentially equal inputs of background sounds and body sounds as modified by the patient's body for common mode rejection of these unwanted background sounds such as respiration or room noise. The sound transducing inputs 24, 26 and 28 are connected to a preamplifier stage 30. The outputs 32 and 34 of the preamplifier stage 30 are connected to two inputs of a differential amplifier stage 36. In the case of dual sound transducer inputs, differential amplifier 36 responds only to the differential heart sound signals and essentially rejects all common mode unwanted signals. In the case of a single sound transducer at 24, the output 34 is amplified by the differential amplifier stage 36. The amplified output 38 of the differential amplifier stage 36 is processed by a filter stage 40 to provide the heart sound signal input 14. The filter stage 40 is arranged to eliminate any frequencies unrelated to first and second heart sounds.

The heart sound signal input 16 is provided by an external amplifier/filter arrangement referred to generally at 42 for use with external sound transducing and amplifying apparatus. The heart sound signal input 18 is provided at the output of a two Khz. cutoff low pass filter stage 44 from a recorded heart sound input 46.

Figure 2:
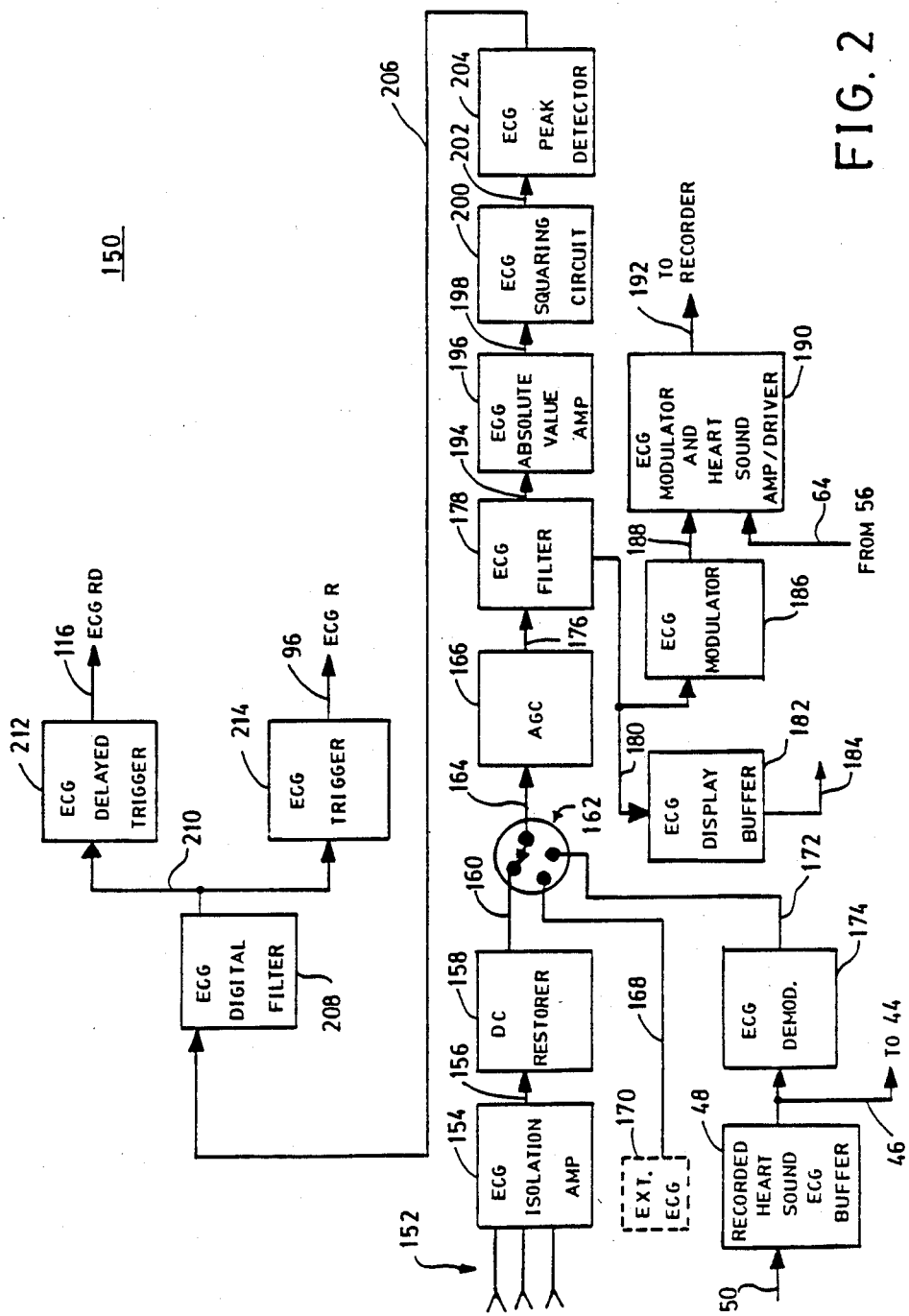
FIG. 2 is a block diagram representation of ECG gating apparatus and recording apparatus of the present invention for use with the heart sound detection and triggering apparatus of FIG. 1.

The recorded heart sound input 46 is provided at the output of a recorded heart sound ECG and buffer stage 48 (see FIG. 2). The input to the recorded heart sound ECG and buffer stage 48 is connected to a playback transducing output 50 of a recorder (FIG. 2). The recorded heart sounds and ECG waveforms of a patient are recorded on a common channel or track by a recording arrangement for use with the present invention for analysis at a time subsequent to actual recording of the heart sounds and the ECG waveform of a patient under investigation for future, further analysis.

The output 20 of the heart sound signal selector switch 12 is connected through a filter stage 52. In a specific embodiment the filter stage 52 is a low pass filter with a cut-off frequency below 500 Hz. which is arranged to eliminate some of the audio signals associated with heart sound transducing but which are unrelated to the actual first and second heart sounds. The output 54 of the filter stage 52 is connected through an AGC amplifier stage 56 to normalize signal levels for the subsequent detection and gating stages of the arragement 10.

A first output 58 of the AGC stage 56 is connected through a heart sound display buffer stage 60 to provide a display output 62 of heart sounds for analysis. A second output 64 of the AGC stage 56 is connected as a summing output for recording along wih ECG waveforms to a recording arrangement as will be discussed in more detail in connection with the ECG gating apparatus of FIG. 2.

The output 64 of the AGC stage 56 is also connected through a positive enveloper and squaring stage 66 which essentially repositions all negative portions of the heart sound waveform at 64 into the positive enveloped signal domain and also squares the input to accentuate the heart sound signals in the positive envelope. The output 68 of the positive enveloper and squaring stage 66 is connected through a comparator or peak detector stage 70 to provide at output 72 a digital trigger signal in response to the heart sounds.

Figure 3:
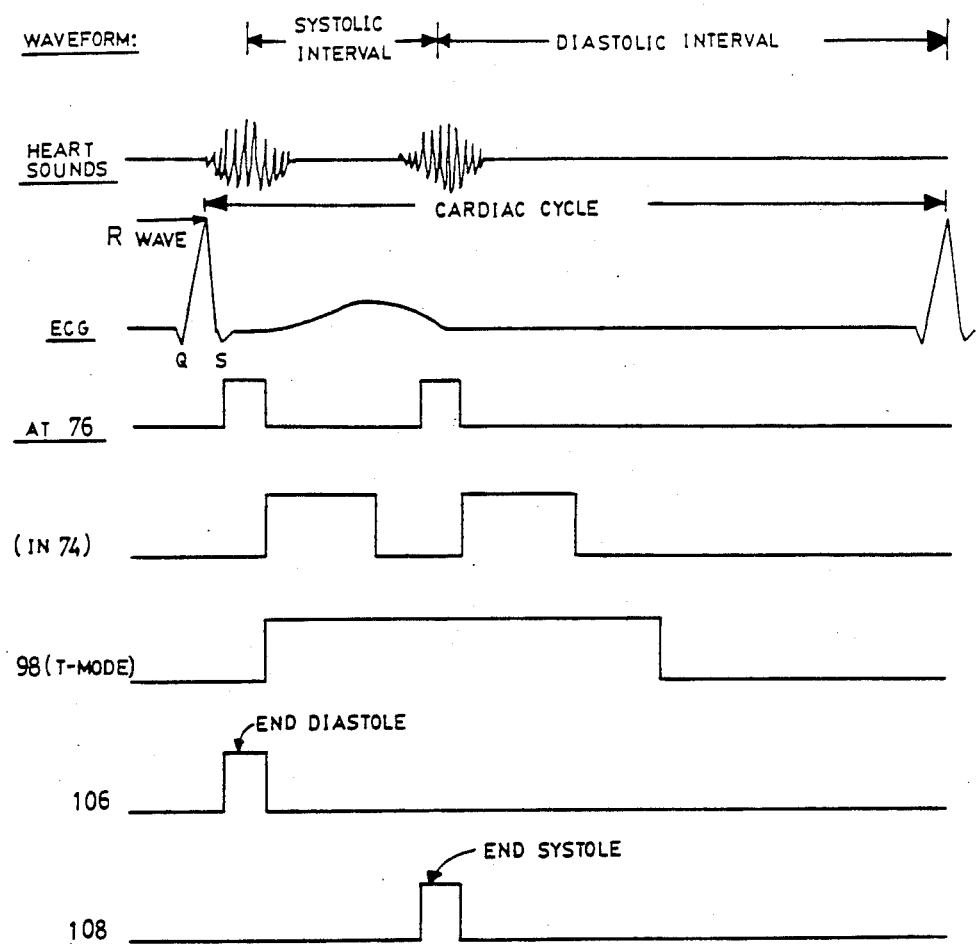
FIG. 3 is a graphic representation versus time of the operation of the heart sound detection and triggering apparatus of FIGS. 1 and 2 in a timed mode of operation and a typical heart cycle illustrating the first and second heart sounds and the ECG waveform associated therewith.

Referring now to FIG. 3, typical first and second heart sounds associated with a typical cardiac cycle are illustrated in conjunction with the ECG waveform with the heart sounds defining the systolic and diastolic intervals of the overall cardiac cycle.

The digital heart sound trigger signals at 72 are connected to a digitally variable digital filter stage 74. The digital filter stage 74 provides pulse shaping and a heart sound signal pulse output at 76 in response to each heart sound trigger signal at 72 in accordance with a digital selection signal at 78. The digital filter stage 74 in accordance with the digital selection signal 78 also provides a variable lock-out time window such that the digital filter is inhibited from outputting additional heart sound signals at 76 within the time interval of the lock-out time immediately after a heart sound signal output at 76.

The digital selection signal 78 is provided by a digital integrator and timing control stage 80 that determines appropriate digital selection signals at 78 in accordance with the cardiac cycle and heart sound timing of the apparatus 10. The digital integrator and timing control stage 80 receives data signals at 82 from a display and control file 84. A data address input 86 is provided to the display and control file from a system timing control stage 88.

The digital heart sound pulse signals at 76 are connected to a window trigger selector stage 92 and a window mode control stage 100. The window trigger selector stage 92 provides a digital trigger control signal at 94 to control operation of a digitally variable time window stage 90 in accordance with either the digital heart sound pulse signal at 76 in a timed mode (T-mode) of operation or an ECG R-wave signal 96 provided as an input to the window trigger selector stage 92 from the ECG apparatus of FIG. 2 in an ECG R-wave (E-mode) of operation.

The trigger selection of the window trigger selector stage 92 is accomplished by a selection input from a selection switch arrangement at 97. In a first E-mode switch state of the arrangement 97, the window trigger selector stage 92 provides a trigger control signal at 94 in accordance with the ECG R-wave signal at 96. In a second T-mode switch state of the switch arrangement 97, the window trigger selector stage 92 provides a trigger control signal at 94 in accordance with the heart sound pulse signal at 76.

The digitally variable time window stage 90 also includes as an input the digital selection signal 78. The digitally variable time window stage 90 sets one or more variable time windows in accordance with the data state of the digital selection signal 78 and the mode of operation as set by switch 97. In accordance with the variable time window or windows, the digitally variable time window stage 90 provides appropriately timed heart sound enable signals at 98 and at 104 to the window mode control stage 100.

The window mode control stage 100 in accordance with the inputs from the heart sound enable signals 98 and 104, and the digital heart sound pulse signals at 76 outputs a first heart sound trigger signal at 106 and a second heart sound trigger signal at 108.

Thus, the digital filter stage 74, the window trigger selector 92, the digitally variable time window stage 90, and the window mode control stage 100 function in combination as a digital time filter as variably set by the digital selection signal 78 to direct the heart sound pulse signals at 76 and distinguish between the first and second heart sounds. The variable time windows are automatically adjusted by the heart sound detection and triggering apparatus 10 to accurately distinguish between the first and second heart sounds for patients with heart rates in a specific predetermined range; e.g., 15–250 beats (heart cycles) per minute in a specific embodiment. The operation of the apparatus 10 to adjust the time window and to detect the heart sounds will be discussed in more detail hereinafter.

The first heart sound trigger signal 106 and the second heart sound trigger signal 108 are provided as inputs to a system trigger select output stage 110 that functions as a selector switch to output a system trigger output signal at 112 for the triggering and control of diagnostic equipment. The trigger select stage 110 also includes the ECG R-wave trigger signal 96 and an ECG R-wave delayed trigger signal 116 as inputs. The signals 96 and 116 are provided from the ECG apparatus of FIG. 2. The system trigger output 112 is also connected through a display trigger stage 118 to provide a display study trigger signal 120 at the appropriate level.

The first and second heart sound trigger signals 106 and 108 respectively and the ECG signals 96 and 116 are also connected as inputs to a display input selection and pulse-to-pulse gate stage 122. The display selection and pulse gate stage 112 includes a selection switch 123 for selecting one of a predetermined number of parameters for display selection as rates (beats per minute) or time intervals (in milliseconds), including, for example, in a specific embodiment first to second heart sounds time interval (F-S), first heart sound to first heart sound time interval (F-F) or (F-F) rate, ECG R-wave to R-wave rate (R-R rate) or time interval (R-R), ECG-R-wave to first heart sound time interval (R-F), ECG R-wave to second heart sound time interval (R-S), and ECG R-wave to R-wave delayed time interval (R-RD) as set on a delay selector. A display 130 discussed hereinafter is controlled by display each of the parameters. The display selection and pulse gate stage 122 responds to the selected trigger signals as set on the selection switch 123 and provides appropriate corresponding timing signals, display signals and mode select signals to provide accurate time interval or rate data for display purposes and also for system control.

Specifically, the display selection and pulse gate stage 122 provides a rate/time interval select output at 124 to appropriately control the system timing control stage 88 in a binary mode corresponding to rate and in a decimal mode corresponding to time interval. The rate/time interval select output 124 is also connected as a selector input to a time interval or rate selector stage 126.

The time interval or rate selector stage 126 outputs display data at 128 to the display 130. The time interval or rate selector stage 126 includes time interval data inputs at 86 from the system timing control stage 88. Further, the time interval or rate selector stage includes rate data inputs at 132. Thus, the time interval or rate selector stage 126 outputs at 128 either the rate data from the rate data input 132 or the time interval data from the time interval data input 86 in accordance with the selector signal at 124. The system timing control stage 88 includes a clock input at 134 from a system timing clock 136. The system timing clock 136 is enabled to output clock pulses at 134 when enabled by a clock enable input 138 from the display selection and pulse gate stage 122. The system timing control stage 88 also includes a preset input at 140 to preset the stage 88 at the start of time interval or rate determination based on the first trigger signal received by the display input and pulse gate stage 122 in accordance with the selected functions. Further, the display selection and pulse gate stage 122 also stops the time interval or rate determination by means of the enable signal 138 to the system timing clock 136.

For example, if the display selection and pulse gate stage 122 is set to the first to second heart sound display selection mode, the system timing control stage 88 will be controlled to start timing interval count data upon the occurrence of the first heart sound pulse signal at 106 and the system timing control stage 88 will stop the count upon the occurrence of the second heart signal. The accumulated count at output 86 then corresponds to the time interval of first to second heart sound signals. The time interval or rate select stage 126 in accordance with a time interval select signal at 124 provides the time interval data at 128 for display.

Considering a rate display, the display and control file 84 is addressed by the data output 86 with the system timing control functioning to count in the rate mode as set by the rate/time select signal 124. In response to the address at 86, the display and control file 84 outputs at 132 the rate data corresponding to the count data address input. With the select signal 124 in the rate mode, the time interval or rate select stage 126 outputs the rate data 132 at the display output 128.

Referring now to FIG. 2 and considering the ECG gating apparatus 150, the ECG input leads generally referred to at 152 include a conventional three lead ECG input from electrocardiogram apparatus including a human ground and the left shoulder and right side patient sensors. The ECG inputs 152 are connected to an ECG isolation amplifier stage 154 that provides a signal at 156 to a DC restorer stage 158. The DC restorer stage 158 is provided to stabilize the DC level of the ECG waveform which commonly experiences disturbances of the DC level. The output 160 of the DC restorer stage 158 is connected as a first selection input to an ECG selector switch 162. The output 164 of the selector switch 162 is connected to an AGC amplifier stage 166.

The ECG selector switch 162 also includes a second input 168 from an external ECG input arrangement at 170. A third input 172 to the selector switch 162 is provided from a recorded ECG signal path. The recorded ECG signal at 172 is provided at the output of an ECG demodulator stage 174. The ECG demodulator stage 174 receives an input at 46 from the recorded heart sound ECG buffer stage 48 from the recorder input 50. The ECG demodulator stage 174 demodulates the recorded ECG signal which is modulated by a 7 Khz. signal (in a specific embodiment) for recording and includes a high-pass filter having a band pass starting at approximately 5 Khz for a specific embodiment of 7 KHz. modulation frequency.

The AGC stage 166 normalizes the selected input at 164 from the selector switch 162 to appropriate levels for the remaining gating circuitry of the ECG apparatus 150. The output 176 of the AGC stage 166 is connected to an ECG filter stage 178 which eliminates unwanted frequency signals associated with the ECG waveform. The ECG filter stage 178 also provides some degree of isolation for the R-wave of the ECG waveform.

The ECG filter 178 provides an output at 180 connected through an ECG display buffer stage 182. The ECG display buffer stage 182 provides an output at 184 for display apparatus to display the ECG waveform.

The output 180 of the filter 178 is also connected through an ECG modulator stage 186 that modulates the ECG waveform at 180 with a 7 Khz. modulation frequency to provide an ECG modulated waveform for recording at output 188. The output 188 is connected to an ECG modulated and heart sound summing amplifier driver stage 190 along with the heart sound signal 64. The summing amplifier and driver stage 190 provides an output at 192 to recording apparatus to record the combined heart sound and ECG modulated waveforms on a common channel or track on an appropriate recording medium such as tape.

The ECG filter stage 178 also provides an output 194 to an ECG absolute value amplifier stage 196. The ECG absolute value amplifier stage 196 transforms or folds the negative portion of the ECG waveform into the positive half and provides processing isolation to account for the possibility of misplaced leads causing false triggers from the ECG waveform from portions of the ECG waveform other than the R-wave.

The output 198 of the ECG absolute value amplifier stage 196 is connected through an ECG squaring circuit 200 to provide an output 202 to an ECG peak detector stage 204. The ECG squaring circuit 200 accentuates the R-wave of the ECG waveform. Thus the ECG peak detector stage 204 receives a waveform to allow appropriate and accurate triggering on the R-wave.

The output 206 of the ECG peak detector 204 is provided to an ECG digital filter stage 208. The ECG digital filter stage 208 provides a lock-out of any non-R-wave triggering signals by providing a lock-out time period on a digital basis for a predetermined period of time following the occurrence of the R-wave. The output 210 of the ECG digital filter stage 208 is connected through an ECG delayed trigger stage 212 to provide the ECG R-wave delayed signal at 116 connected as an input to the display selection stage 122. The output 210 of the ECG digital filter stage 208 is also connected through an ECG trigger stage 214 to provide the ECG R-wave trigger signal 96.

Considering the operation of the heart sound detection and triggering apparatus 10 in more detail and referring again now to FIGS. 1 and 3, with the trigger mode selection switch in the time or T-mode, the distinction between the first and second heart sounds is accomplished based solely on the timing relationships between the heart sound signals at 76. When using the terms first and second heart sounds, reference is being made respectively to the end diastole and end systole sounds. To avoid confusion, the following discussion will use the terms diastole heart sound and systole heart sound to differentiate from the first occurring heart sound and subsequent heart sounds at 76.

When operation of the detection process commences in the T-mode for each heart cycle, the digital filter stage 74 is set by the digital selection signal 78 to provide a lock-out or inhibit window of time equal to the shortest systolic time interval for the file value selected in the display and control file 84.

The apparatus 10 begins the detection process for each heart cycle starting with file values for the maximum heart rates to be detected. This procedure ensures that the heart sounds will be properly detected and that no valid heart sounds will be missed due to the inhibit window in the filter stage 74 being too long. With the filter stage 74 set to provide an inhibit time of the shortest systolic interval for the maximum heart rate, no valid systole heart sound will be inhibited or missed if the first pulse at 76 from a heart sound and the second pulse at 76 from a heart sound occur with the shortest systolic interval.

Upon the occurrence of a first pulse at 76, that may correspond to either diastole (first heart sound) or systole (second heart sound), the digital filter 74 inhibits signals at 76 due to false or extraneous heart sounds.

In response to the heart sound signal pulse at 76 and the heart sound enable signal at 98, the window mode control stage 100 provides a pulse signal at the first heart sound trigger output 106.

After the termination of the brief heart sound signal pulse at 76 resulting from a first received heart sound (which could be diastole or systole), the digitally variable time window stage 90 enables the heart sound signal at 98 for a predetermined window of time as variably selected by the selection signal 78 from the digital integrator and timing control stage 80 in accordance with the file value addressed at 86 and output at 82 from the display and control file 84.

At this time, the file value corresponds to the diastolic interval of the maximum heart rate. This window of time characterized by the enable time of signal 98 is the safe period of time within which to interrogate for the second heart sound (systole) without erroneously detecting a diastole pulse if the heart rate of the patient being monitored is a maximum. This window of time at 98 also corresponds to a systolic interval which is substantially greater than the systolic interval for the maximum heart rate.

If a second heart sound occurs at 76 during the enable time of the window enable signal at 98, the window mode control stage 100 provides a second heart sound trigger pulse signal at 108. Thus, in this example, the second heart sound received corresponds to systole and the first heart sound received corresponded to diastole.

If no heart pulse signal at 76 occurs during the window enable time of the signal 98, either the first heart sound received was systole or the heart rate is substantially lower than the maximum rate first set for interrogation by the digital integrator and timing control stage 80.

The detection process proceeds with the digital integrator increasing the enable window time at 98 and the inhibit window time of the digital filter 74 in data steps and in a predetermined manner according to the file table in stage 84. At some point along the descending table, the first heart sound detected will be diastole and the second heart sound detected will be systole and will occur within the enable window time of the signal at 98. In accordance with the actual heart rate of the patient being interrogated, this procedure might encompass several heart cycles.

The file table data in the display and control file of stage 84 is selected to provide a predetermined number of table ranges to cover the entire range of heart rates to be interrogated from the maximum heart rate to the minimum heart rate.

Considering now operation of the heart sound detection and triggering apparatus 10 in the ECG R-wave triggered mode (E-mode), the occurrence of the ECG R-wave signal at 96 via the window trigger selector conditions the digitally variable time window stage 90 to provide a first heart sound enable time window at 98. The first heart sound enable time window in the E-mode is a fixed time interval throughout the detection process. The digital filter 74 after the occurrence of a heart sound at 76 provides a variable inhibit window time in accordance with the selection signal at 78 as in the T-mode.

Upon the occurence of a first received heart signal pulse at 76 in the E-mode within the enable time of signal 98, the window mode control stage 100 outputs a first heart sound trigger signal at 106 in response to the heart sound pulse at 76 and the first heart sound enable signal 98. Further, a second heart sound enable signal at 104 is enabled for a variably programmed window time via signal 78. In a specific embodiment, the second heart sound enable signal at 104 is provided after the termination of the first heart sound enable signal at 98 rather than after the occurrence of the first heart sound pulse at 76 or the first heart sound signal at 106.

The variable time enable window provided by the signal 104 is set by the digital integrator 80 and the file table in stage 84 to be equal to the allowable maximum diastolic interval for the file table values being interrogated at the time. For example, at the start of the detection process, the maximum heart rate is possible and thus the maximum diastolic interval corresponds to the diastolic interval for the maximum heart rate.

Upon the occurrence of a heart sound pulse at 76 occurring after the window inhibit time of the digital filter 74, the window mode control stage 100 provides the second heart sound pulse trigger signal at 108 if the heart sound signal at 76 occurs within the enable time window set at 104. If the heart sound pulse at 76 does not occur within the enable time at 104, the apparatus 10 proceeds to move through the file table in a predetermined manner until the second heart sound is detected within the enable time window at 104 with successively longer enable windows being established as the process continues until proper detection occurs.

After proper detection occurs, the apparatus 10 continues to detect the first and second heart sounds and provides on the display 130 a read-out of the time interval or rate of the function selected on the display selection switch 123. If the heart rate of the patient varies during the detection process after proper detection has occurred, the display and control file stage 84 and the digital integrator stage 80 are addressed in accordance with the previous time interval at 86 to appropriately vary the control time windows to maintain proper detection. If proper detection sequence or synchronization is lost due to rapid heart rate change or false input conditions, the apparatus 10 reestablishes proper detection or synchronization in the same manner in which original detection was achieved as discussed hereinbefore.

Referring now to FIG. 4 wherein identical reference characters and numerals refer to corresponding elements and stages of FIG. 1, a specific embodiment of the heart sound detection and triggering apparatus 10 to achieve the objects of the heart sound detection and triggering apparatus 10 will now be discussed. Considering now the digital filter stage 74 (FIG. 4g), the digital selection signal 78 including the form control leads W1 through W4, is connected to control the respective stages of a four stage analog switch 250. The analog switch stages of 250 in accordance with the selection signal 78 selectively connect one or more resistors in the resistor array 252 from a reference supply to the timing input of a monostable stage 254. The time period of the monostable is thus selected in accordance with the selection signal 78 by one or more of the resistors in the array 252 being connected in parallel to the timing input. The heart sound signal at 72 from the comparator stage 70 is connected to trigger a monostable stage 256. the $\overline{Q}$ output of the stage 256 is connected at 258 to one input of a two-input AND gate 260 with inverting input logic, thus functioning as a NOR gate. The output of the gate 260 is the digital heart sound signal 76. The second input 262 of the gate 260 is connected to the Q output of the monostage 254. The output of the gate 260 is also connected to the negative trigger input of the monostable stage 254.

The window trigger selector stage 92 includes a first two-input AND gate 263 with inverting input logic with a first input being connected to an E gate signal. The second input of the gate 263 is connected to the $\overline{Q}$ output of the monostage 254. A second two-input AND gate 264 with inverting input logic includes a first input connected to a T gate signal. The second input to the gate 264 is connected through a resistor to the ECG R-wave signal 96. The outputs of each of the gates 263 and 264 are respectively connected to one input of a two input NOR gate 266. The output of the NOR gate 266 is the trigger select signal 94. The T gate signal corresponds to the timed mode of operation and the E gate signal corresponds to the ECG R-wave triggered mode of operation for heart sound detection. The T gate and E gate signals are provided by means of the switch 97 which functions in the E (ECG R-wave) mode to ground the T gate signal and correspondingly in the T (time) mode to ground the E gate signal.

The digitally variable time window stage 90 (FIG. 4h) includes a first window stage. The first window stage includes a four stage analog switch device 268 and a monostable stage 270. The control signal from each of the respective four stages in the analog switch device 268 selectively controls the connection of one resistor in the array 272 to the timing input of a monostable stage 270. The trigger select signal 94 is connected to a negative trigger input of the monostable stage 270. The control inputs of the stages of the analog switch device 268 are respectively controlled by logic gates in a logic gate array 274 such that the respective W1 through W4 inputs of the selection signal 78 control the device 268 in the T mode. In the E mode of operation, the E gate signal controls a predetermined fixed selection of the resistor array 272.

The Q output of the monostable stage 270 in the first window stage provides the heart sound enable signal 98(Q) and the $\overline{Q}$ output of the monostable stage 270 provides the heart sound enable signal 98($\overline{Q}$). The enable signal 98($\overline{Q}$) is connected to the positive trigger input of a monostable stage 276 in a second time window stage of the digitally variable time window stage 90. The timing of the monostable stage 276 is controlled at a timing input by a four stage analog switch device 278. The selection of one or more resistors in a resistor array 279 is controlled by the data selection signal 78 including the W1 through W4 control lines at the control input of the switch device 278.

The $\overline{Q}$ output of the monostage 276 provides the second heart sound and enable signal 104 utilized in the E mode of operation. In the T mode, the enable signal 98($\overline{Q}$) is utilized as a second heart sound enable signal. In the E mode of operation, the heart sound enable signal 98(Q) is utilized as a first heart sound enable signal and the enable signal 104 is utilized as a second heart sound enable signal by the window mode control stage 100.

The window mode control stage 100 (FIG. 4i) includes a first heart sound enable logic gate array 280 and a second heart sound enable logic gate array 282. The first heart sound logic gate array 280 includes a two-input AND gate 284 with inverting input logic operable in the T mode and a second two input AND gate 286 with inverting input logic operable in the E mode. One input of the T mode gate 284 is connected to the enable signal 98(Q) and the second input is connected to the E gate signal. A first input of the gate 286 is connected to the enable signal 98($\overline{Q}$) and the second input is connected to the T gate signal. The outputs of the gates 284 and 286 are respectively connected to one input of a two-input NOR gate 288 of the first heart sound enable array 280.

The second heart sound enable logic array 282 includes a first two-input, T mode AND gate 290 with inverting input logic and a second two-input, E mode AND gate 292 with inverting input logic. The first input of the T gate 290 is connected to the enable signal 98($\overline{Q}$) and the second input is connected to the E gate signal. A first input of the gate 292 is connected to the heart sound enable signal 104 and the second input is connected to the T gate signal. The outputs of the gates 290 and 292 are respectively connected to one input of a two-input NOR gate 294. The output of the gate 288 is connected to one input of a three-input AND gate 296 with inverting input logic. The second input to the gate 296 is connected to the $\overline{Q}$ output of a false prevention, flip-flop stage 300. The third input of the gate 296 is connected through a resistor to the output of an inverter gate 302. The input to the inverter gate 302 is provided by the heart sound signal 76. The output of the inverter gate 302 is also connected to the second input of the gate 298. The output of the gate 298 is connected through an inverter gate to provide the second heart sound trigger pulse signal 108. The output of each of the gates 296 and 298 is respectively connected through output driver stages to provide additional external output trigger signals in addition to and independent of the trigger select stage 110 that provides the selected, main system trigger output at 112.

Figure 4C:
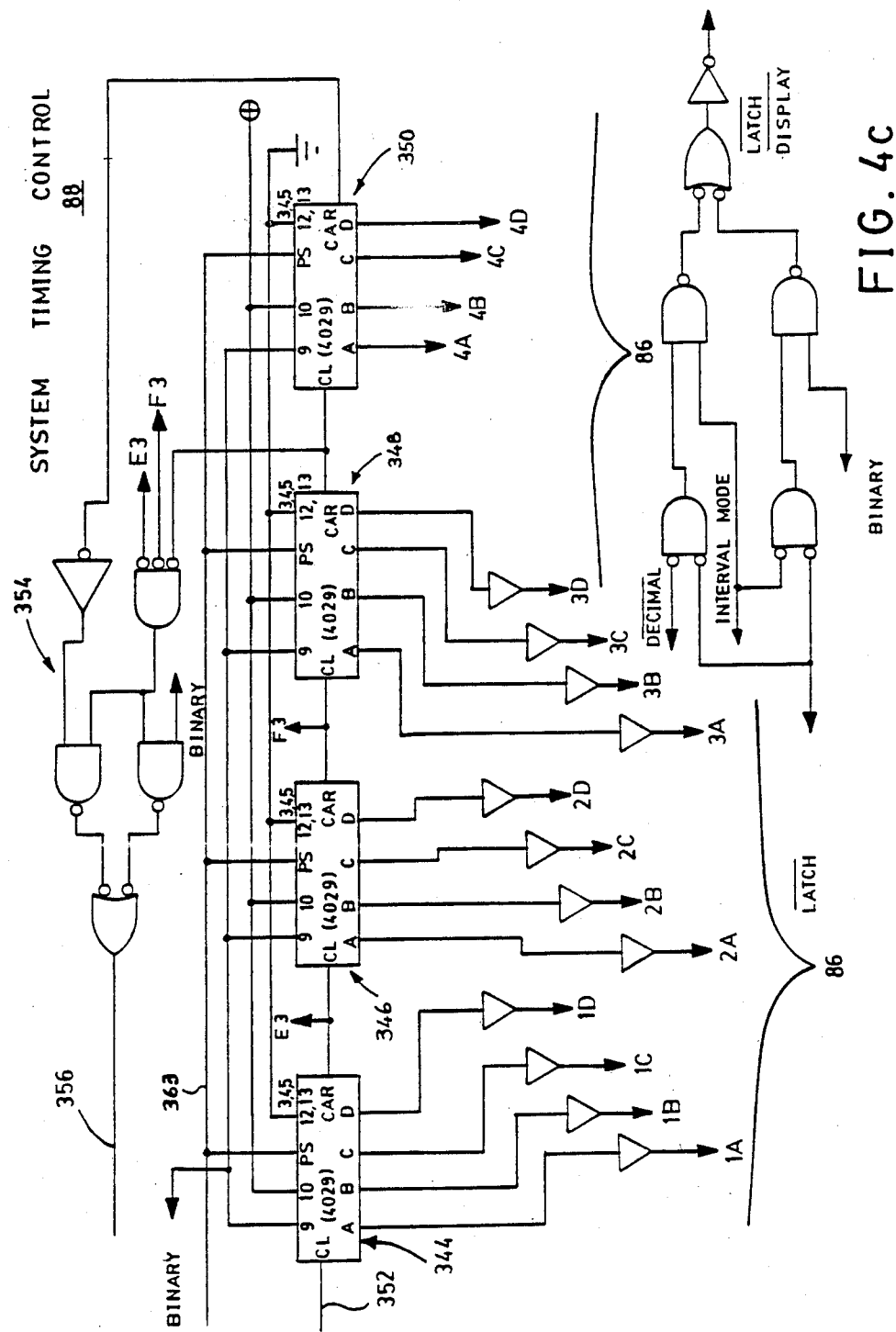
Figure 4D:
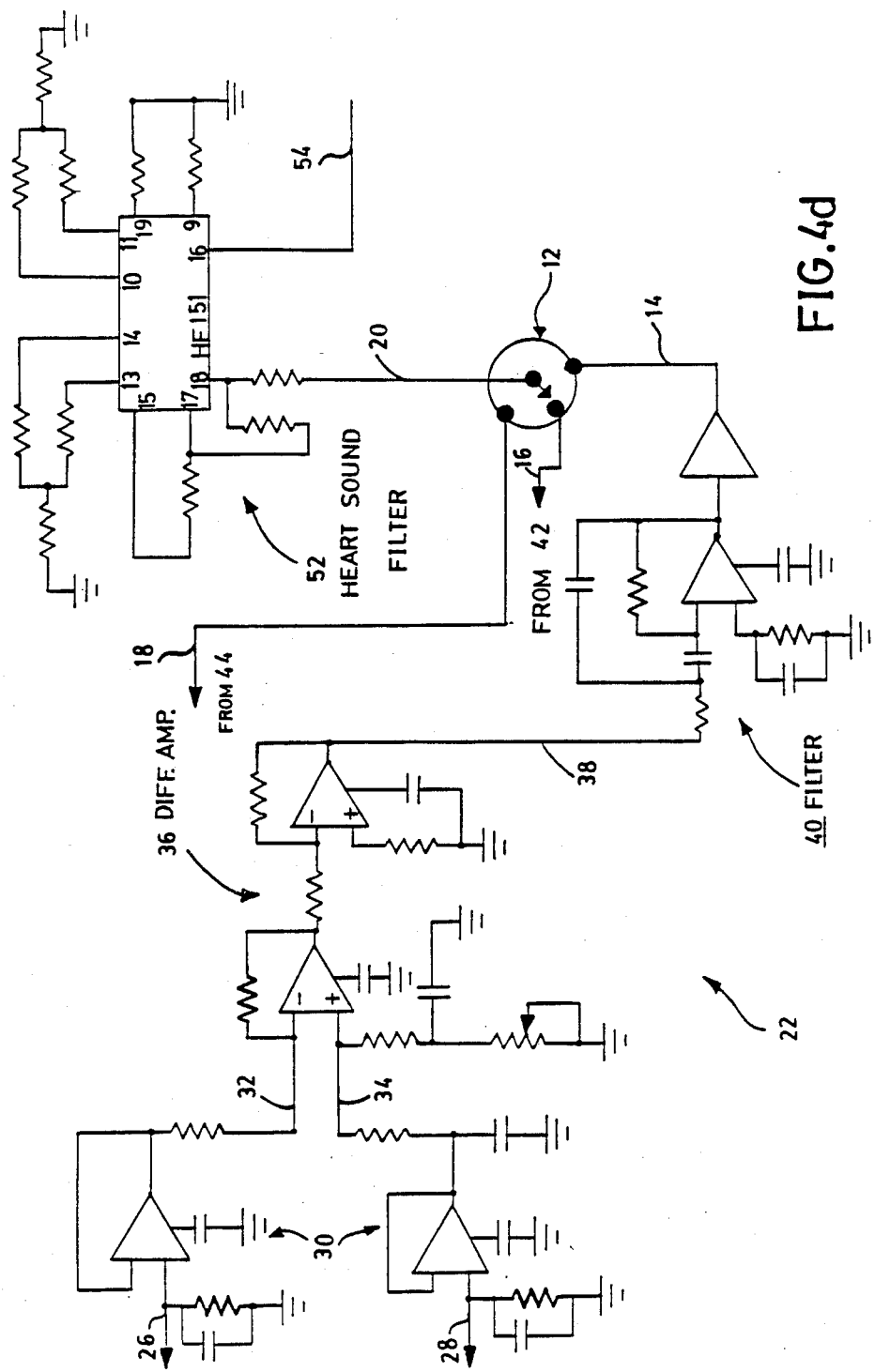
Figure 4E:
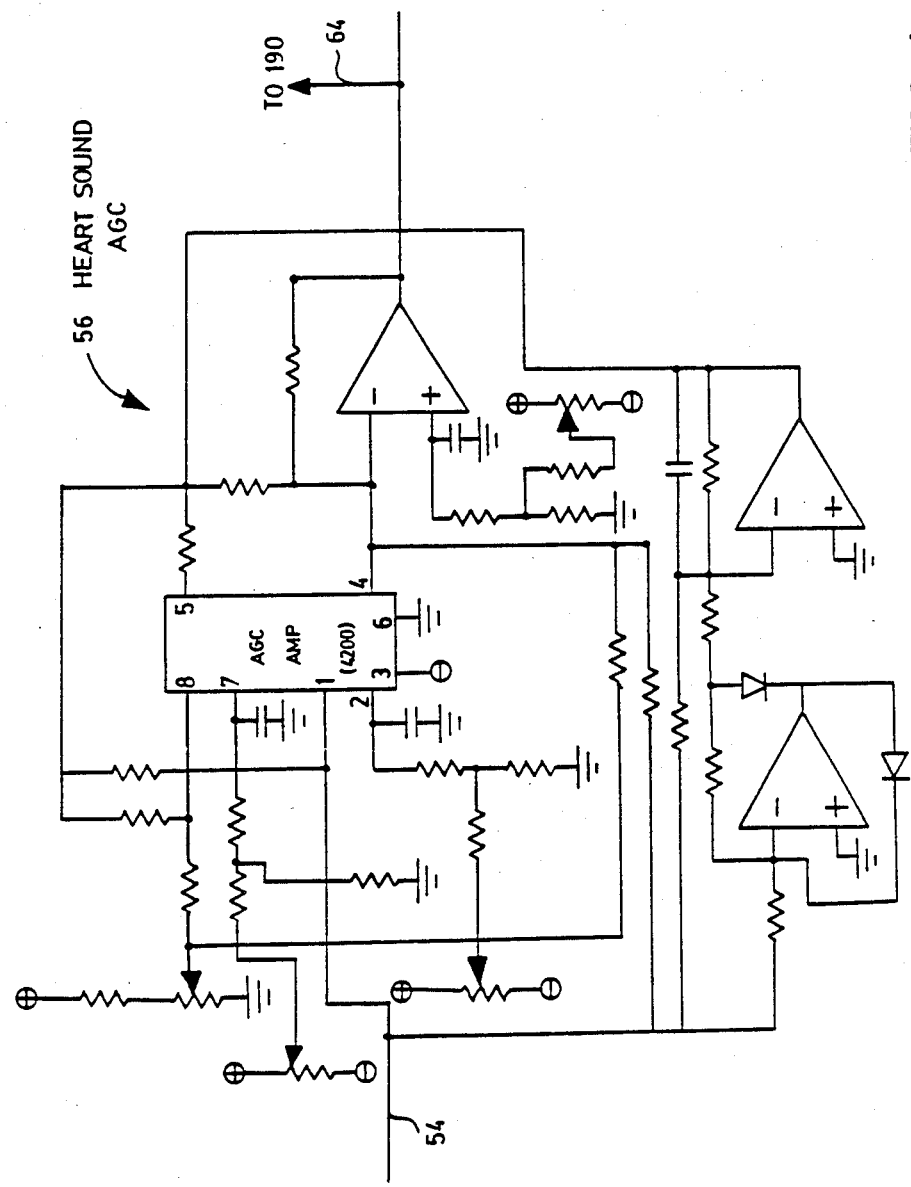
Figure 4F:
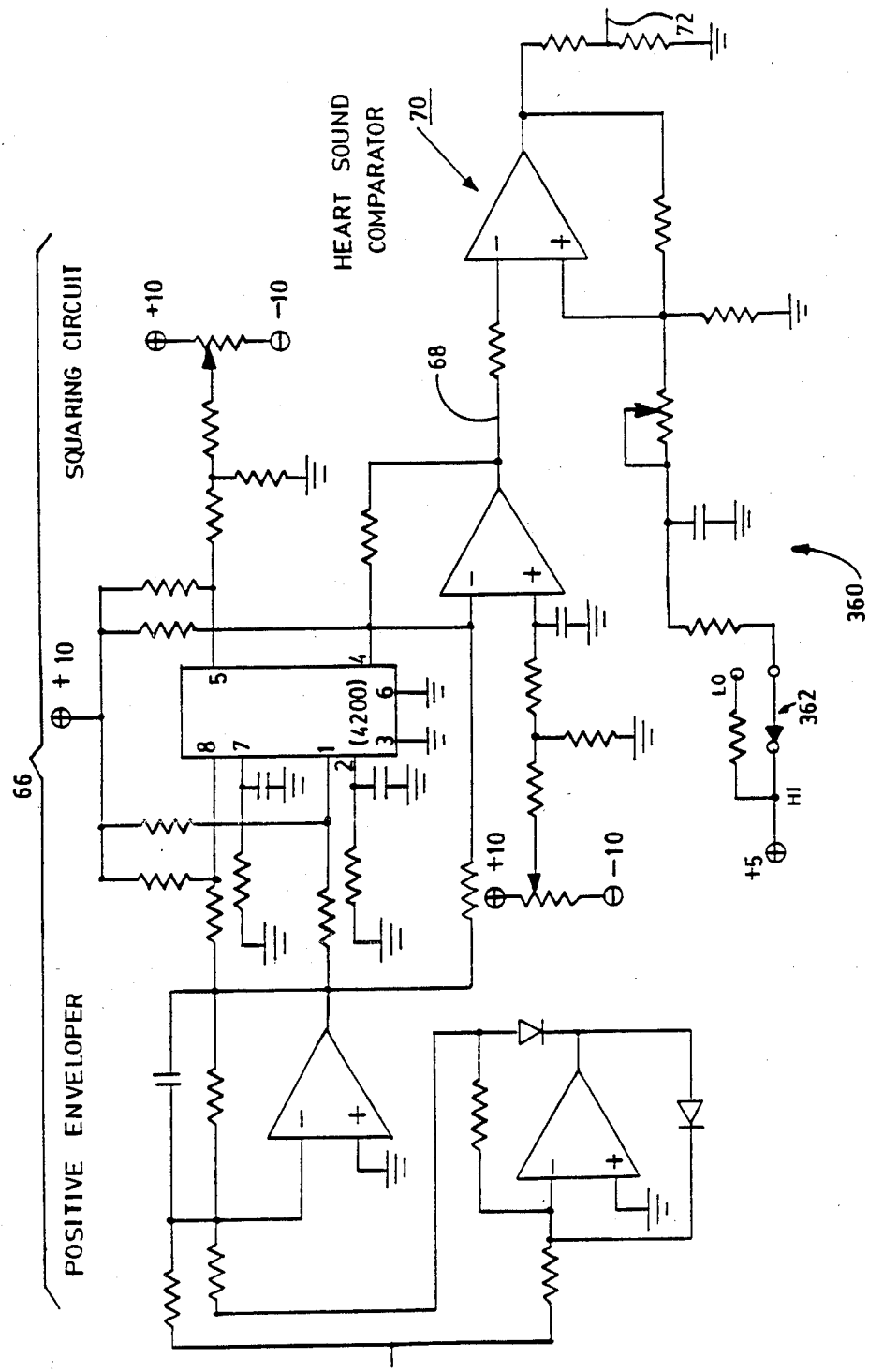
Figure 4G:
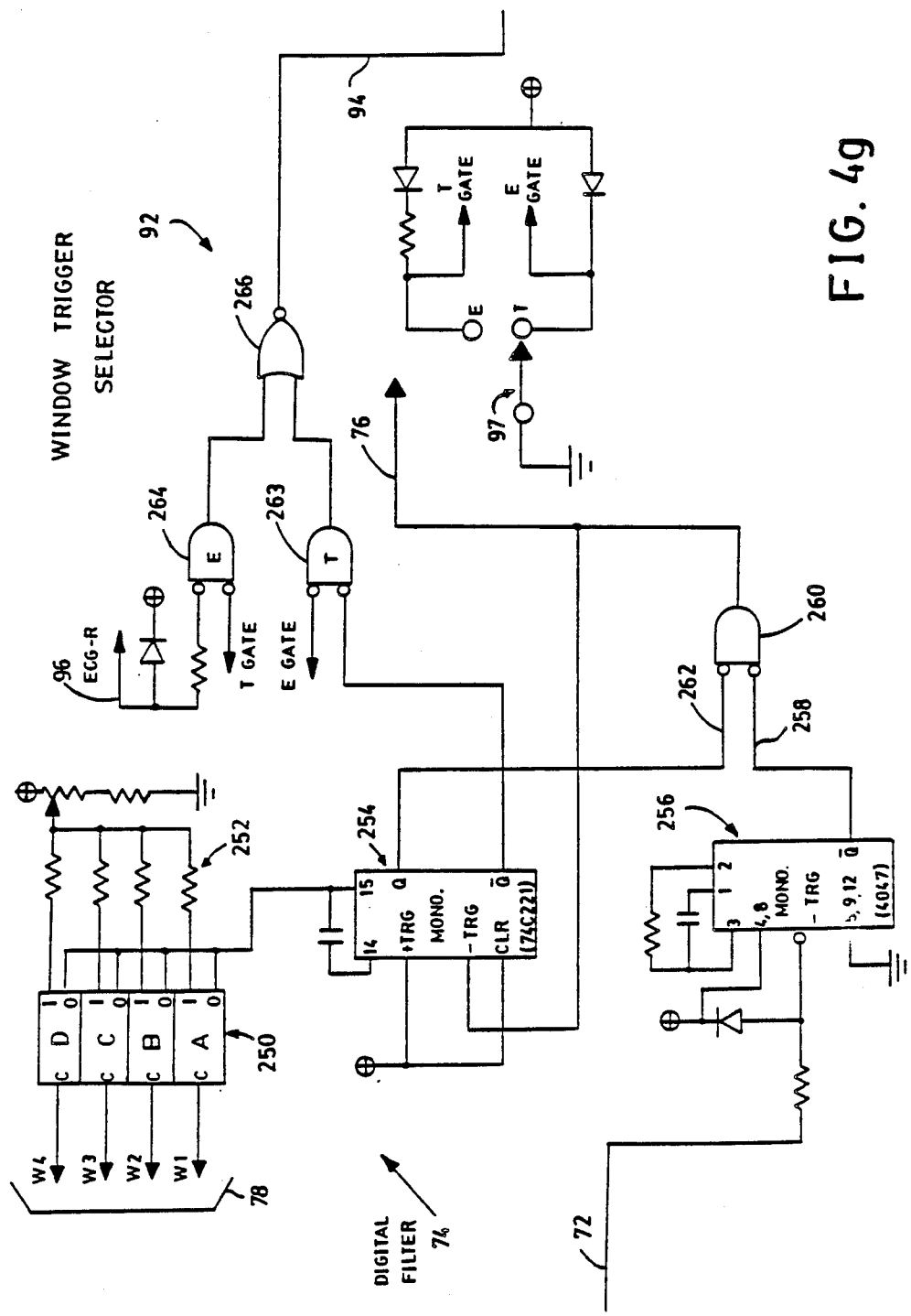
Figure 4H:
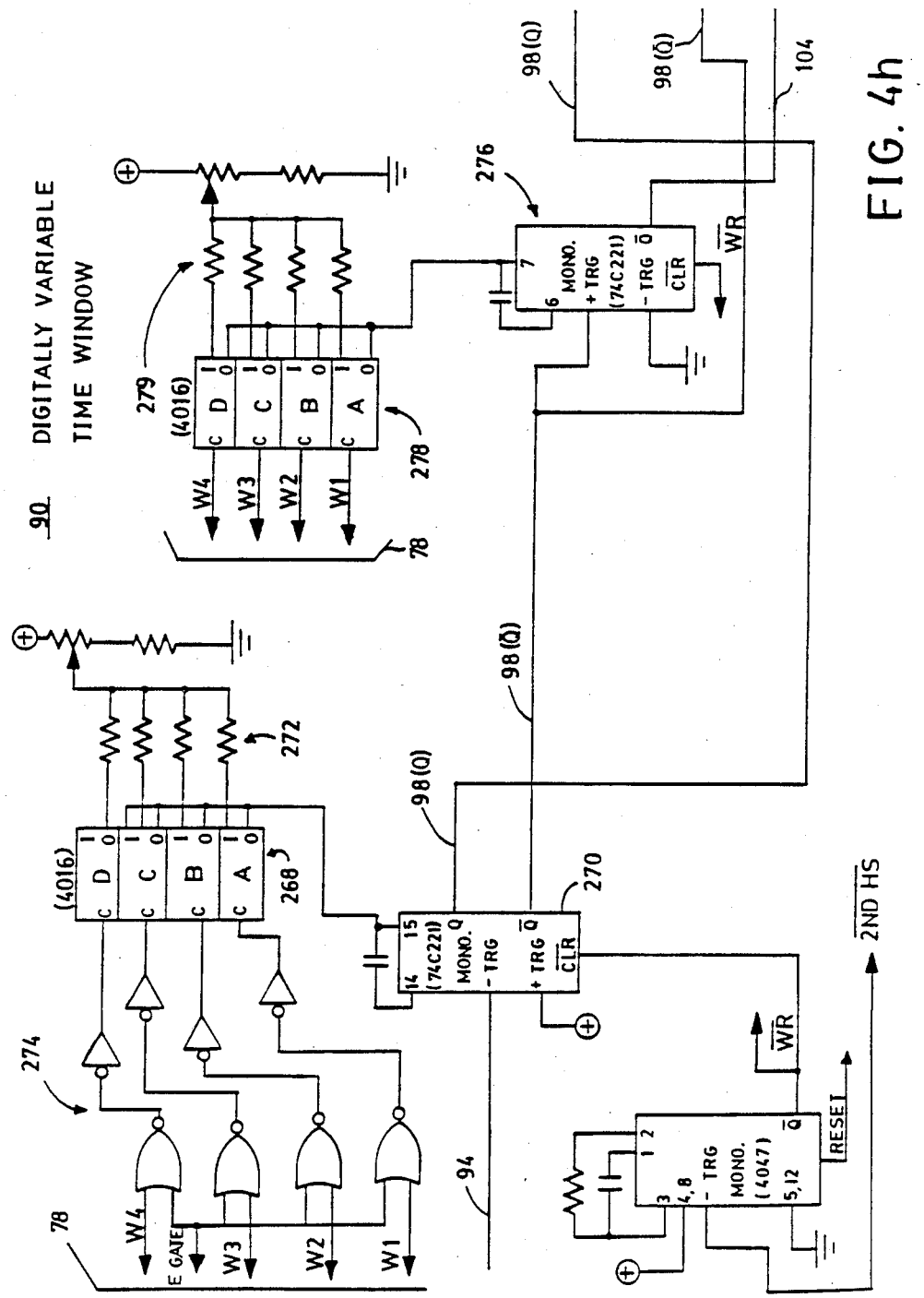
Figure 5:
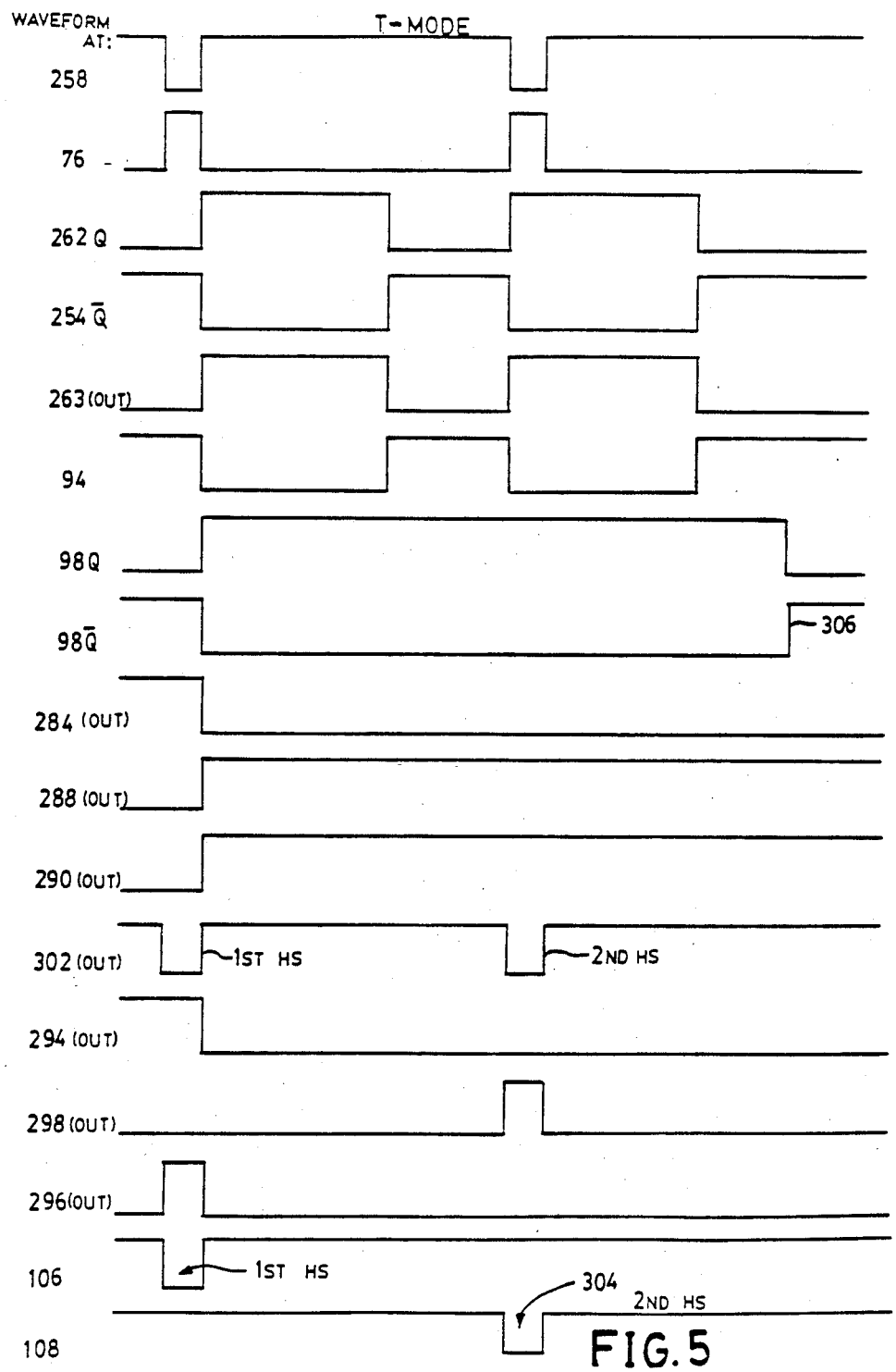
FIG. 5 is a representation of various timing diagrams and signal relationships in the specific embodiment of the heart sound detection and triggering apparatus of FIG. 4 regarding a first to second heart sound timing detection mode of operation.

Considering now the operation of the heart sound detection and triggering apparatus 10 in the T mode operation wherein first and second heart sounds are detected based on the timing between the first and second heart sounds and referring now to FIG. 5, the T gate signal is high and the E gate signal is low with the selector switch 97 in the T mode position. Upon the occurrence of a heart sound signal at 72 from the comparator 70 (FIGS. 1 and 4f), the monostable stage 256 (FIG. 4g) of the digital filter stage 74 is triggered.

Upon the triggering of the monostable stage 256, the heart sound pulse signal at 76 provides a high level pulse signal that triggers the monostable stage 254 of the digital filter 74 on the falling edge of the pulse signal at 76. With the monostable stage 254 triggered, the Q output at 262 provides a high level lock-out window signal to inhibit additional heart sound signals from 72 during the variably selected lock-out window inhibit time via selection signal 78. As discussed hereinbefore, the lock-out inhibit time is the shortest systolic interval for the file table value of operation presently being interrogated as selected from the digital integrator 80 and the display and control file 84.

The monostable stage 254 at the $\overline{Q}$ output also enables the T gate 263 and thus the gate 266 to provide the trigger select enable signal 94 to the digitally variable time window stage 90.

The trigger enable signal 94 triggers the monostable stage 270 (FIG. 4h) to provide at the 98Q and 98$\overline{Q}$ outputs the program timing window signals to enable second heart sound detection with the timing window being variably determined by the selection signal 78. The enable signal 98(Q) disables further first heart sound detection via gates 284, 288 and 296 (FIG. 4i). The enable signal 98($\overline{Q}$) through gates 290, 294 and 298 provides a second heart sound enable signal.

During the window time in which the gate 294 provides an enable signal through the gate 298, if a second heart sound signal at 76 is received, the output of the gate 298 through the inverter gate will provide a second heart sound pulse trigger signal at 108 as shown in FIG. 5 at 304. As discussed above, if no second heart sound occurs during the variable window time for detecting a second heart sound the 98$\overline{Q}$ signal changing state at 306 in FIG. 5, no second heart sound will be detected.

The time of enablement for detection of the second heart sound after the occurrence of the first heart sound is set to the longest diastolic interval for the table file value being interrogated as determined by the display and control file 84 in accordance with the timing input 86 from the system timing control 88.

Figure 6:
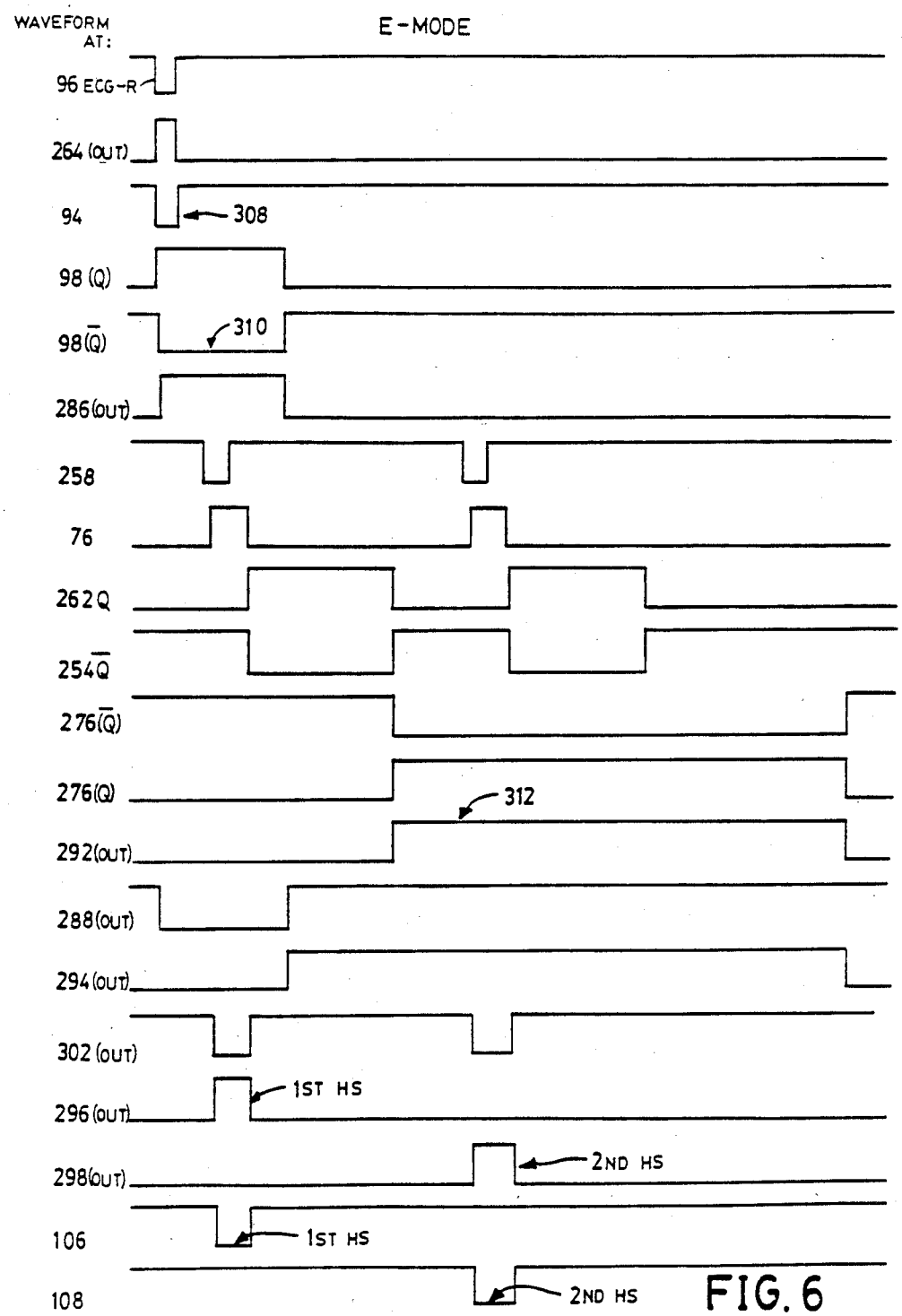
FIG. 6 is a representation of various timing diagrams and signal relationships in the specific embodiment of the heart sound detection and triggering apparatus of FIG. 4 regarding an ECG R-wave detection mode of operation.

Considering now the E mode of operation of the heart sound detection and triggering apparatus 10 and referring to FIG. 6, with the trigger selection switch 97 in the E mode position, the T gate signal is low and the E gate signal is high. Upon the occurrence of the ECG R-wave signal at 96 at the gate 264 (FIG. 4g), a trigger select signal 308 (FIG. 6) at 94 is provided through the gates 264 and 266. The pulse signal 308 at 94 triggers the monostable stage 270 (FIG. 4h) to provide a time enable window 310 (FIG. 6) at the 98($\overline{Q}$) output for a fixed time interval set in the E mode by the E gate signal through the logic gate array 274, the switch device 268 and the resistor array 272. It should be understood that in discussing the various monostable stages, a respective timing capacitor of fixed value is also utilized in addition to the resistor arrays 252, 272 and 279 (FIGS. 4g and 4h) to provide the various time constants.

The 98$\overline{Q}$ signal along with the T gate signal enables the gate 286 and thus the gate 288 (FIG. 4i). Accordingly the gate 296 will provide a first heart sound signal at 106 (FIG. 6) upon the occurrence of a heart sound signal at 76. As before when a heart sound signal at 72 from the comparator 70 triggers the monostable stage 256 (FIG. 4g), a heart sound signal at 76 is provided.

Further, upon the occurrence of a signal at 76, the monostable stage 254 (FIG. 4g) of the digital filter stage 74 is triggered to provide a lock-out inhibit window time as variably set by the selection data 78 to inhibit further heart sound signals at 72 if they occur during the inhibit window time. The inhibit window time is set to the shortest diastolic time for the table value being interrogated by the apparatus 10.

After the time-out of the enable window provided by the monostable stage 270 (FIG. 4h) for the first heart sound enable, the 98($\overline{Q}$) signal triggers the monostable stage 276. Thus the monostable stage 276 at the $\overline{Q}$ output provides a second heart sound enable signal 104 for the variably set time window 312 (FIG. 6) to enable gates 292 and 294. Further the gates 284 and 288 are now disenabled by the time-out of the window signal at 98($\overline{Q}$) and thus the first heart sound enable logic gate array 280 is disabled from producing further heart sound pulses.

During the enable time window 312, if an additional heart sound pulse occurs after the window inhibit time provided by the monostable stage 270 (FIG. 4h), the gate 298 (FIG. 4i) is enabled to provide a second heart sound signal 108 (FIG. 6).

Considering now operation of the display and control file 84 in accordance with the system timing control stage 88 and the digital integrator and timing control stage 80, the following Table A depicts an illustrative example of one specific embodiment of the apparatus 10 for appropriate heart detection. Table A describes the ranges of operation to accurately detect the heart sounds and to avoid missing or falsely detecting heart sounds; e.g. a first occurring heart sound as systolic and a second occurring heart sound as diastolic which would result in an erroneous determination. The first column entitled W1–W4 Digital Input at 78 includes the range of 0 through 15 and represents the binary data on the selection input 78 as output from the digital integrator and timing control stage 80 to program the timing windows of the monostable stages 254 and 276 in the E mode of operation and the timing windows of stages 254 (FIG. 4g), 270 and 276 in the T mode of operation.

The second column of Table A entitled "Window Times at 270, 276 of [the digitally variable time window stage] 90" depicts in milliseconds the window times set at monostables 270 and 276 in the time mode and window set in monostable stage 276 in the E mode. The second through seventh columns represent the values in milliseconds. The second column represents the various time windows corresponding to the digital selection data in the first column. The fifth column entitled "Window Time [monostable stage] 254 of [digital filter stage] 74" depicts the variable window time settings corresponding to the W1 through W4 digital inputs at 78.

course it should be understood that various other specific ratios could be utilized if desired.

With these parameters established for a specific embodiment, the seventh column corresponds to the data signal at 86 from the system timing control 88 at which

TABLE A

| W1-W4 DIGITAL INPUT AT 78 | WINDOW TIMES AT 270,276 OF 90 (A) | HEART PERIOD A/.333 | HEART PERIOD (A + 70)/.666 | WINDOW TIME 254 OF 74 (B) | HEART PERIOD (B + 20)/.333 | ADDRESS 86 TO 84 | DATA AT 82 TO 80 |
|---|---|---|---|---|---|---|---|
| 0 | NO OPERATION | | | | | → 4096 | |
| 1 | 1329 | 3987 | 2098 | 587 | 1821 | → 2519 | → 1 |
| 2 | 980 | 2940 | 1575 | 433 | 1359 | → 1626 | → 2 |
| 3 | 559 | 1677 | 943 | 248 | 804 | → 1233 | → 3 |
| 4 | 508 | 1524 | 867 | 226 | 738 | → 981 | → 4 |
| 5 | 365 | 1095 | 652 | 162 | 546 | → 824 | → 5 |
| 6 | 332 | 996 | 603 | 147 | 501 | → 696 | → 6 |
| 7 | 263 | 789 | 499 | 117 | 411 | → 612 | → 7 |
| 8 | 242 | 726 | 468 | 108 | 348 | → 538 | → 8 |
| 9 | 203 | 609 | 409 | 91 | 333 | → 492 | → 9 |
| 10 | 192 | 576 | 393 | 86 | 318 | → 447 | → 10 |
| 11 | 167 | 501 | 355 | 76 | 285 | → 420 | → 11 |
| 12 | 162 | 486 | 348 | 72 | 276 | → 390 | → 12 |
| 13 | 144 | 432 | 321 | 64 | 252 | → 367 | → 13 |
| 14 | 138 | 414 | 312 | 62 | 246 | → 342 | → 14 |
| 15 | 124 | 372 | 291 | 56 | 228 | ↓ | → 15 |

In the specific example represented in Table A for various ranges of operation in accordance with file table values in the display and control file 84, the third and fourth columns labeled respectively "Heart Period A/0.333" and "Heart Period (A+70)/0.666" represent the extremes of allowable operations for each corresponding window time of operation in column two and the digital selection value in column one.

For example, considering the table entry corresponding to the W1 through W4 input 7, with a window time of 263 milliseconds for the monostable stages 270 and 276 in the T mode operation, the value 789 milliseconds derived by A/0.333 corresponds to the period of the lowest heart rate for which the window enable time of 263 milliseconds will provide detection of the systolic heart sound if the first heart sound that occurs is diastolic. The fourth column entry 499 milliseconds derived from (A30 70)/0.666 corresponds to the heart period for the maximum heart rate for accurate operation within the setting of W1 through W4 at 7 with the longest permissible window equal to 263 milliseconds to avoid improper detection from a first occurring systolic signal and a second occurring diastolic heart sound signal. The column 6 entry 411 milliseconds derived from (B+20)/0.333 with an inhibit window of the digital filter 74 of 117 milliseconds corresponds to the period of the maximum heart rate that can be detected based on the shortest systolic heart pulse after the occurrence of a diastolic heart pulse. For the values in Table A, a ratio of systolic interval equal to one-third of the overall heart cycle and a ratio of diastolic interval equal to two-thirds of the heart cycle are utilized. Of the display and control file 84 will be controlled to output at 82 the appropriate address for the range of operation to the digital integrator stage 80.

Figure 7:
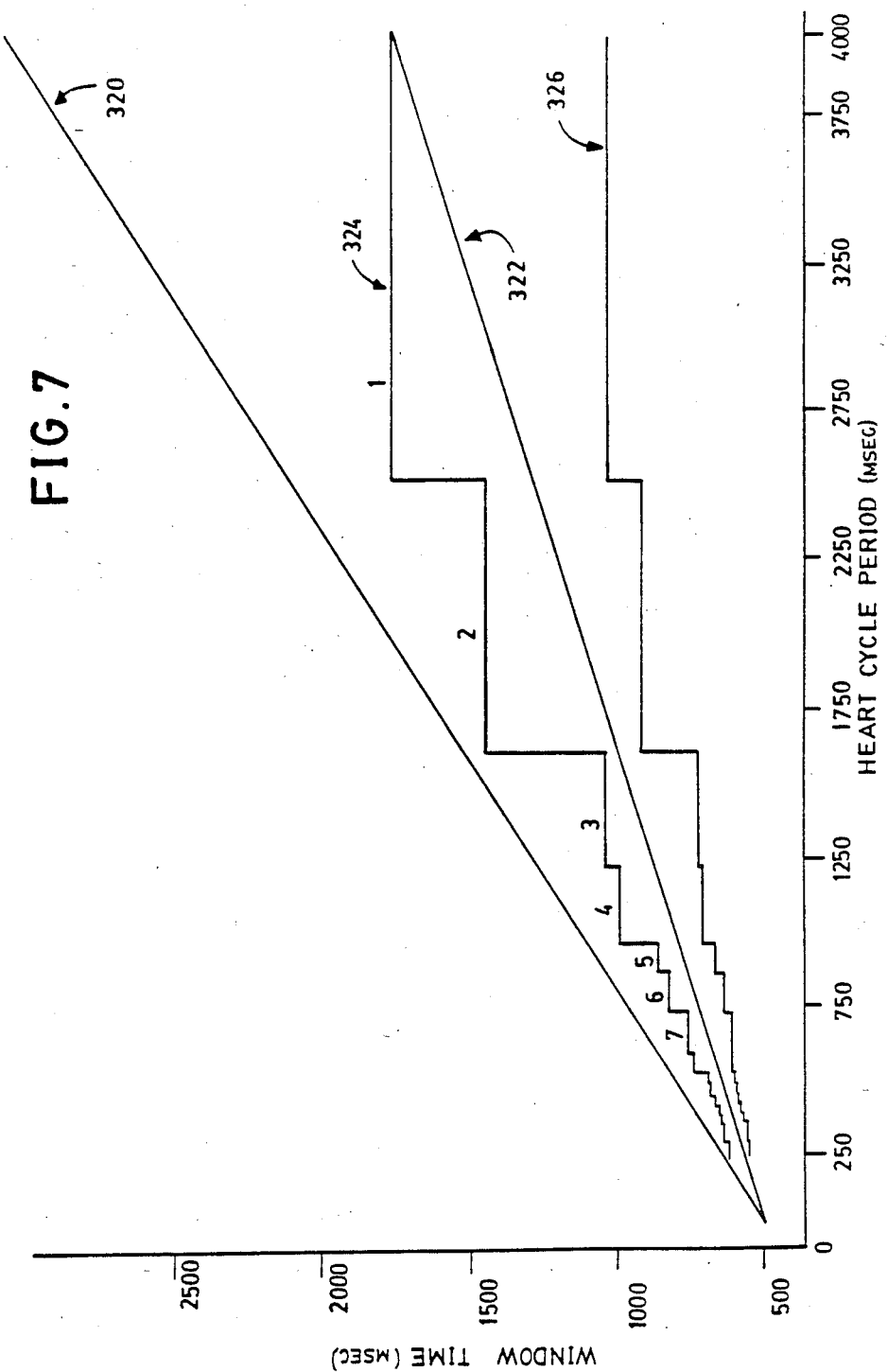
FIG. 7 is a graphical representation useful in illustrating the operation of the present invention of FIG. 4 and illustrating look-up table ranges of operation for setting timing windows in connection with heart sound detecting.

Referring now to FIG. 7, the appropriate window enable times for the various monostables 270, 276 and 254 (FIGS. 4g and 4h) are graphically depicted along with the selected window times of operation in the specific embodiment for a selected corresponding range of heart cycle period for appropriate operation. For example, the area between the upper inclined line 320 and the lower inclined line 322 represent permissible enabled window times for the monostable stage 270 in the T mode and the monostable stage 276 in the E mode relative to the corresponding heart cycle periods along the horizontal axis. The actual lines from the E mode are slightly offset due to the ECG-R signal 96 (FIG. 6) time of generation. The upper steps or staircase depiction 324 represents the window enable times for the monostable stage 276 in the E mode and the monostage 270 in the T mode for the specific implementation to practice the present invention in accordance with Table A. The lower steps or staircase depiction 326 graphically illustrates the window enable times for the ranges of operation in Table A in a specific implementation for the monostable stage 254 (FIG. 4g) of the digital filter 74. The window times corresponding to the digital input at 78 with values 1 through 7 are indicated in a relatively accurate manner while the remaining 8 through 15 window enable ranges are only approximately indicated due to the accuracy of the graphic scale.

In accordance with FIG. 7, the line 320 represents the relationship between maximum period of heart rate that can be appropriately detected for the corresponding window time while the lower line 322 represents the minimum heart cycle period at which the corresponding intersecting window enable time will accurately distinguish between first and second heart pulses without false indications. Thus, the lower line 322 corresponds at each entry to the enable window time approximately equal to the diastolic interval for the heart cycle period.

Referring now again to FIG. 4j and considering the display and control file stage 84, two INTEL type 2732 ROM stages 330 and 332 are provided in the specific implementation that are addressed by the system time and control data signals 86. In response, the ROM stages 330 and 332 output respective portions of the rate display data signals 132 to the timing interval or rate convert select stage 126 and the data range signals 82 to the digital integrator stage 80. Referring now to the eighth column of Table A entitled Data at 82 to 80, the data on the lines 82 as listed in Table A corresponds to the address ranges at 86 from column 7 of Table A; i.e. the data at column 8 is output corresponding to the upper and lower ranges of the address data 86. For example, if the address 86 from the system timing control stage 88 outputs a count equal to a value between 824 and 981, the display and control file stage 84 at output 82 provides binary data equal to 5.

The digital integrator stage 80 (FIG. 4i) is implemented by a four stage adder device 334, a four stage flip-flop device 336, J-K flip-flop stage 338, an inverter gate 340, and a two input AND gate 342. The digital integrator 80 is arranged to output the data signals at W1 through W4 at 78 from the respective $\bar{Q}$ outputs of the four stage, flip-flop device 336. The range data signals 82 from the display and control file 84 (FIG. 4j) are connected to the A input of each stage of the four stage adder device 334. Further the Q outputs of each stage of the flip-flop device 336 are respectively interconnected to the B inputs of the four stage adder device 334. The sum outputs of the second, third and fourth adder stages of device 334 are respectively connected to the D input of the first, second and third flip-flop stages of device 336. The carry output of the fourth adder stage is connected to the D input of the fourth flip-flop stage of device 336. The sum output of the first adder stage is connected to the J input and is also connected through an inverter gate 340 to the K input of the flip-flop 338. The clock of the flip-flop 338 is connected to the output of the gate 342. The inputs to the gate 342 are a latch signal and a binary signal.

In operation, the digital integrator stage 80 is arranged to provide at data output 78 on lines W1 through W4 a value equal to one-half of the sum of the previous output at 78 plus the data input at 82. The summing operation is performed upon each clock to the device 336 provided by the latch and binary signals through the AND gate 342.

The system timing control stage 88 (FIG. 4c) includes four counter stages 344, 346, 348 and 350 that are arranged in cascade to provide the count data output 86 with respective data outputs 1A through 1D from counter 344, 2A through 2D from counter 346, 3A through 3D from counter 348, and 4A through 4D from counter 350. The input to the cascaded counter stages 344, 346, 348 and 350 is connected at the clock input of counter 344 from the output 352 of the system timing clock oscillator stage 136 (FIG. 4b). The system timing clock stage 136 is enabled by the enable signal 138 from the logic devices of the display input selection and pulse-to-pulse gate stage 122.

The system timing control stage 88 also includes an overflow inhibit arrangement 354 (FIG. 4c) provided by an array of logic gates to provide a full scale stop signal at 356. The full scale stop signal 356 is connected in the display input selection stage 122 to disable operation of the system timing clock 136 (FIG. 4b) via the enable signal 138.

Consider now the operation of the apparatus 10 (FIG. 1) as illustrated by a typical example of heart sound detection with the selection switch 123 including switch poles 123a, 123b and 123c (FIG. 4a) of the display input selection stage 122 being set to the one position for first to second heart sound operation and with the trigger selection switch 97 (FIG. 4g) in the T mode. Operation of the apparatus 10 commences with the data selection 78 providing an output representing the digital number 15 so as to set the window time of the monostable stage 270 (FIG. 4h) to 124 milliseconds and the window inhibit time of the monostable stage 254 (FIG. 4g) to 256 milliseconds. The operation of the apparatus 10 commences as described hereinbefore assuming maximum heart rates to insure proper detection being established by a procedure as follows.

Assuming that the heart rate of the patient being monitored is not within the range 15 in Table A corresponding to the heart period being greater than 372 milliseconds, the display input selection stage 122 (FIG. 1) will enable accumulated counting in accordance with the clock input of the system timing stage 88 upon the occurrence of the first heart sound signal 106 remembering that this first heart sound pulse at 106 may be either diastole or systole as will be determined.

If the heart rate is slower than a period corresponding to 372 milliseconds, no second heart sound at 108 will be detected by the apparatus 10 and the counters 344, 346, 348 and 350 (FIG. 4c) will accumulate counts to cause a full scale stop to be generated at 356 wherein the binary signal at 360 will be generated and the output to the display and control file 84 (FIG. 4j) at 86 will be a full scale 4,096 count. In response, the display and control file 84 for the next detection cycle will output a binary 1 representation to the digital integrator stage 80 (FIG. 4i) via data lines 82. In response the digital integrator stage 80 at 78 will output a binary value 8 to condition the window time of monostable stage 270 (FIG. 4h) to a 242 millisecond value and a window inhibit time of 108 milliseconds for the monostable stage 254 (FIG. 4g). In this next cycle of operation, the system timing control 88 (FIG. 4c) again begins counting upon the occurrence of a first occurring heart sound and if the heart rate is slower than a period equal to 726 milliseconds, the second heart sound will not be detected and the display and control file stage 84 (FIG. 4j) will be controlled to again output a one binary value at 82 to the digital integrator stage 80 (FIG. 4i). In response, the digital integrator stage 80 will output a four binary value at 78 and condition the monostable stage 270 (FIG. 4h) to provide a window enable time of 508 milliseconds and a window inhibit time for monostable 254 of (FIG. 4g) of 226 milliseconds. Thus, operation continues throughout the ranges of operation of Table A until heart sound detection is achieved. For faster heart rates, a fewer number of detection cycles are required in order to achieve synchronization for proper detection.

Once proper heart sound detection is achieved in one of the various ranges of operation, a first heart sound being diastole will start the counting in the system timing stage 88 (FIG. 4c) and the second heart sound signal at 108 (FIG. 4a) will stop the counting. Thus in each such cycle, the data value at 86 represents the time interval from the first to second heart sounds as provided to the timing interval or rate convert select stage 126 (FIG. 4j). Further the display input selection stage 122 (FIGS. 4a, 4b) will be in a decimal mode of operation and the select line 124 (FIG. 1) will condition the time interval rate selector stage 126 to provide the time interval data 86 to the display 130 via the selector output 128 (FIG. 4j). Thus the correct first to second heart sound time interval will be displayed as a read out by the display 130 for each cycle of detection. The display 130 is also provided with a heart beat indicator to indicate by a short on-time the heart rate of the patient for clarification purposes. The apparatus 10 includes a heart beat stage 357 (FIG. 4i) to provide the heart beat signal to drive the display indicator. Further, the operator by means of a CRT display and the heart sound trigger signals at 359 and 361 (FIG. 4i) can view the actual heart sound signal timing to confirm that proper detection is being achieved.

After proper heart detection is established within the range of operations spanning typical heart rates from 15 to 250 beats per minute (heart cycles per minute), the display will provide the first to second heart time interval and the time interval at 86 will appropriately address the display and control file 84 to control the range of operation of the apparatus 10 through the digital integrator stage 80. For example, if synchronized heart detection is achieved in range 8 of operation of the Table A, and the next succeeding detection cycle results in a time interval at 86 equal to 450 milliseconds, the display and control file 84 will output a data value 10 to the digital integrator stage 80 and the selection data at 78 will control operation in range 9 (see FIGS. 1, 4i and 4j).

Concerning other display input selection modes, the switch levels 123a, b and c (FIGS. 4a) appropriately connect the corresponding trigger signal inputs to provide the first and second trigger signals to the input selection stage 122 in each of the eight positions to provide an appropriate determination of the rate or time interval function selected.

Figure 4I:
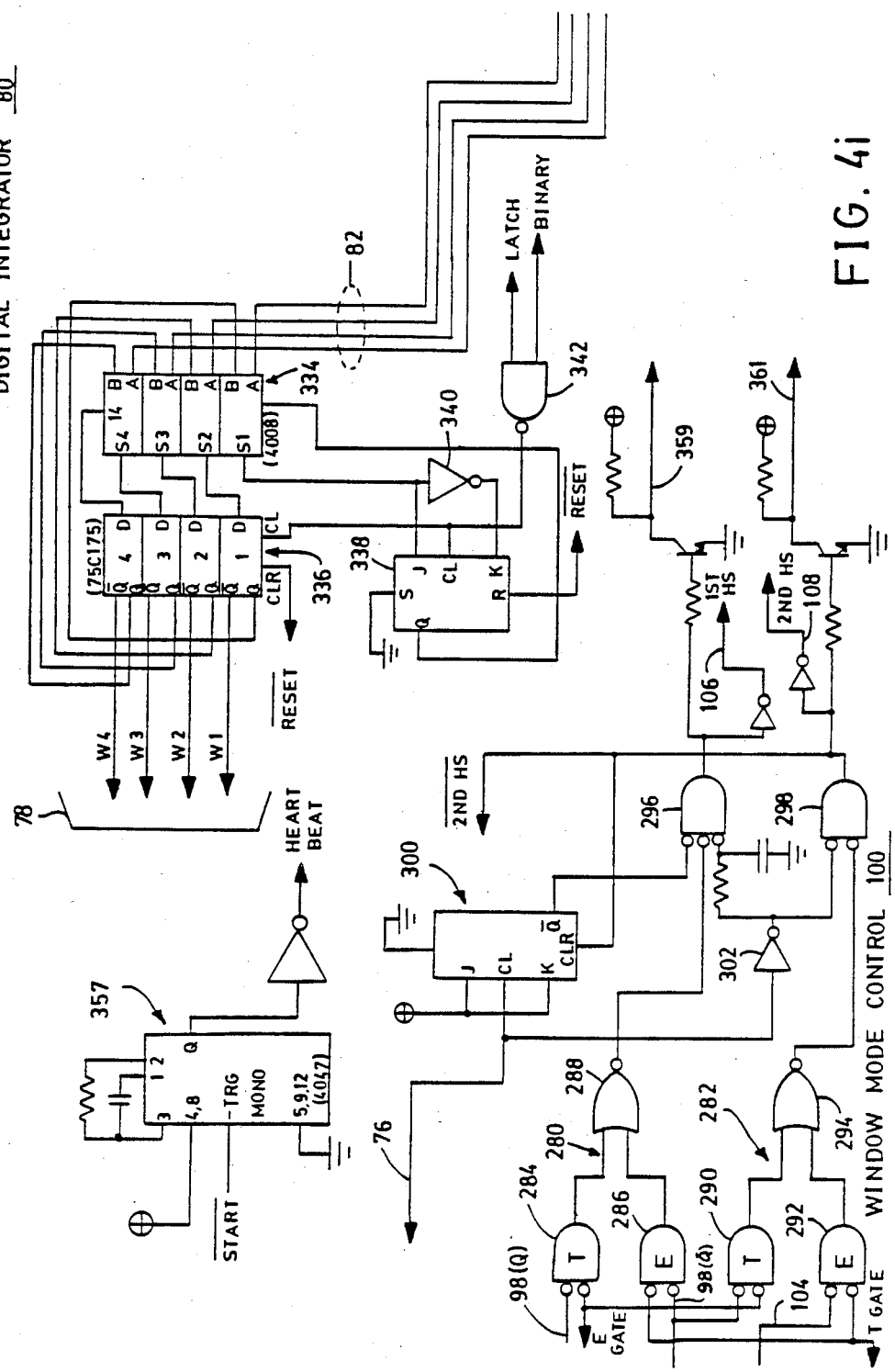
Figure 4J:
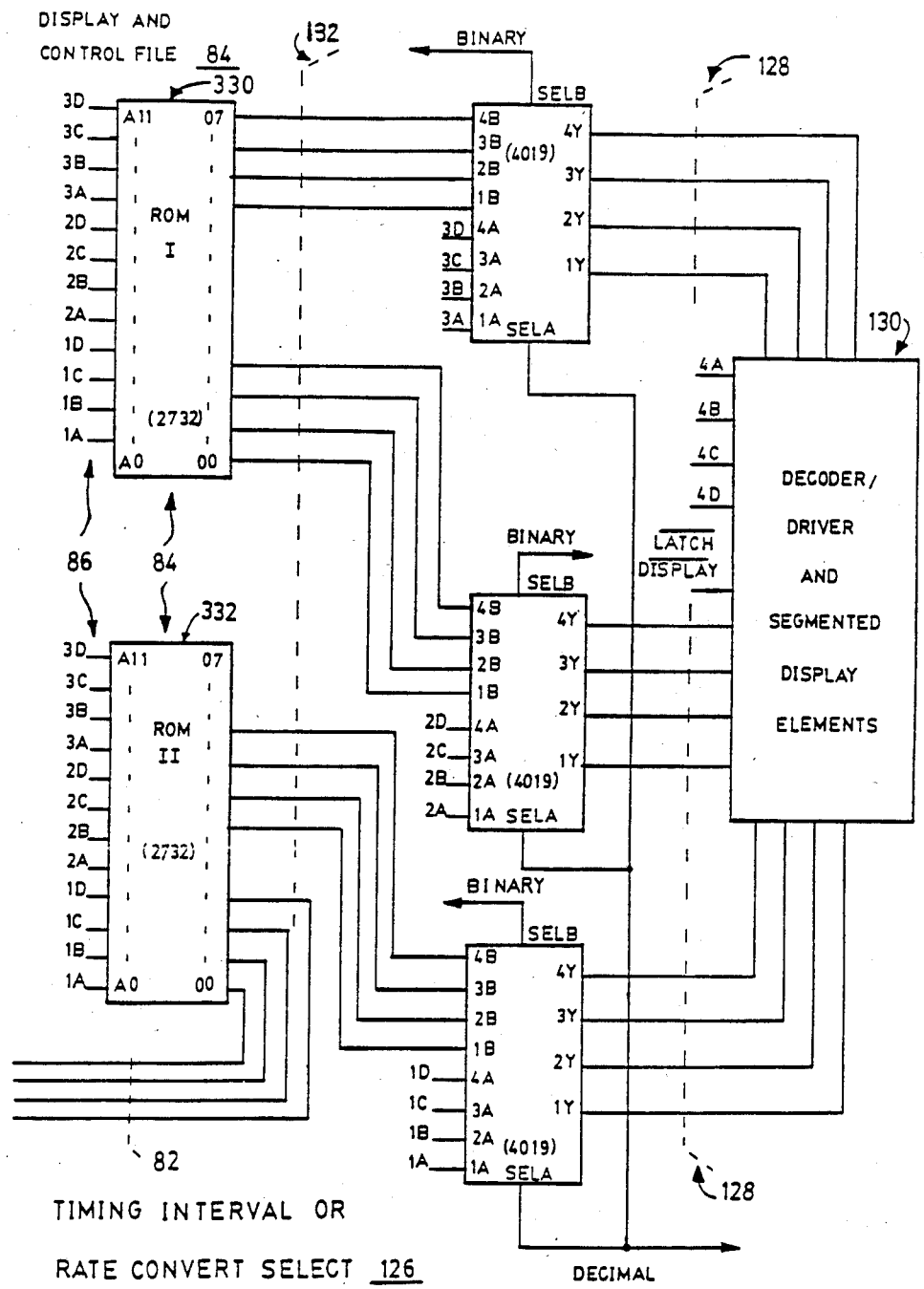

A heart sound threshold setting arrangement 360 is provided in the heart sound comparator stage 70 (FIG. 4f). In the specific embodiment of FIG. 4, a hi or low threshold setting switch 362 is provided. Thus, the level of the heart sound signal at 68 to produce the digital heart sound signal at 72 can be selected by the threshold setting arrangement 360. In other specific embodiments, the comparator 70 is arranged to produce the heart sound signal at 72 at predetermined portions of the heart sound signal at 68. For example, in one specific embodiment, the comparator 70 is arranged to provide the signal at 72 on the upward, rising slope of the signal at 68. In another specific embodiment, the comparator is arranged to provide the signal at 72 on the downward, falling slope of the signal at 68.

Further, while the generation of the heart sound trigger pulse signals at 106 and 108 of FIG. 4 (FIG. 4j) have been described as occurring coincident with the heart sound signal pulse at 76 (FIG. 4g), it should be realized that in other specific embodiments the stages 74, 92, and 100 (FIGS. 4g, 4j) are arranged to generate the trigger pulse signals at 106 and 108 in accordance with other predetermined time relationships with respect to the heart sound signals at 72, 258 and 76 (FIG. 4g) to achieve the desired time of generation of the heart sound trigger pulse signals at 106 and 108.

Figure 8:
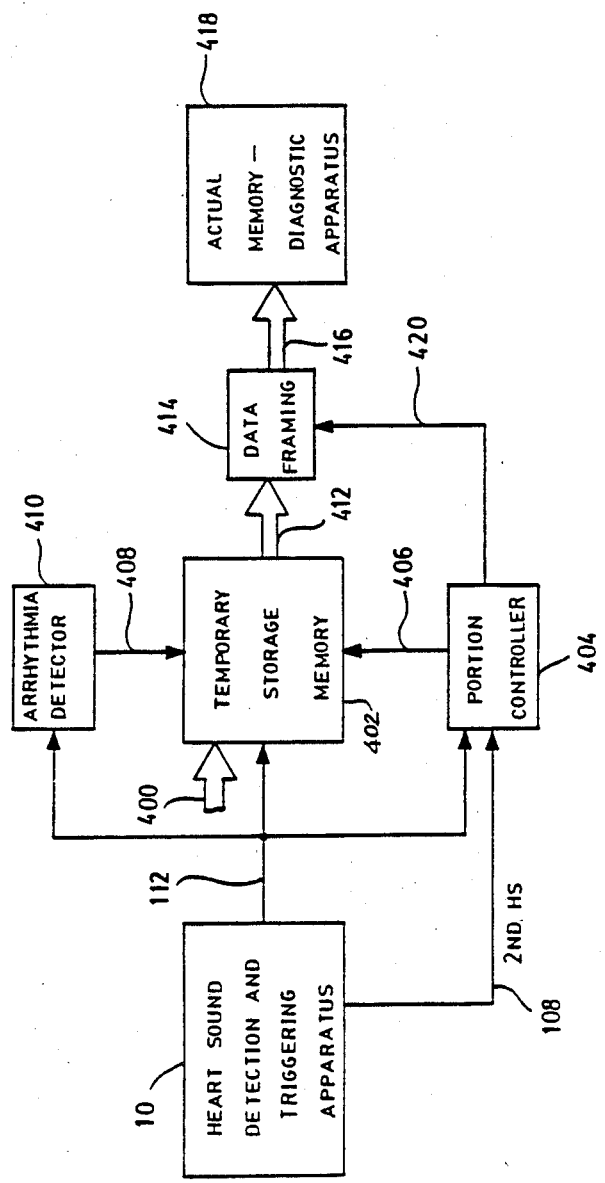
FIG. 8 is a block diagram representation of diagnostic apparatus for use with the present invention and illustrating the control of diagnostic apparatus in accordance with the present invention.

Considering now one arrangement for the control of diagnostic apparatus in accordance with the present invention and referring now to FIG. 8, cardiac data at 400 from cardiac analysis apparatus (not shown) is connected to the data input of a temporary storage (scratchpad) memory 402. The data at 400 represents particular cardiac analysis data for evaluating cardiac performance; e.g. blood pool studies or blood pool volume date from radiation detection apparatus such as a scintillation camera.

The temporary storage memory 402 receives data at 400 as a function of time and stores the accumulated data in selected time interval frames. The selected time intervals are sufficiently short to ensure appropriate analysis at a desirable number of points. For example, in blood pool studies including ejection fraction determination and volume curves it is essential to acquire data representing appropriate stopaction image data of the heart and to analyze the data at the appropriate times in terms of heart function operation. Thus, the data acquisition frames or time intervals must be short enough to satisfy all desirable analysis criteria. For example, data frames of 10 milliseconds or less are required in specific analysis arrangements in connection with rapid heart rates.

In order to appropriately select the stored image data for analysis, a portion controller 404 is provided that outputs an address control signal at 406 to select the portion of the data frames in the temporary storage memory 402 that is determined to be required for appropriate and accurate data analysis of the cardiac functions being analyzed.

The portion controller 404 in a specific-embodiment receives as inputs the second heart sound signal trigger 108 and a system trigger signal 112 from the heart sound detection and triggering apparatus 10 to determine the appropriate data frames.

In a preferred embodiment, the temporary storage memory 402 is also controlled by a data control signal 408 provided as an output from an arrhythmia detector 410. When the arrhythmia detector 410 determines that the data in the temporary storage memory 402 corresponds to a heart cycle that represents invalid or confusing data, the data control signal 408 functions to cause the temporary storage memory to erase the data.

The arrhythmia detector 410 includes the system trigger signal 112 as an input for determining whether or not a present heart cycle represents an arrhythmia cycle and should be disregarded for data analysis purposes. In specific embodiments, the arrhythmia detector 410 interrogates the first heart sound to first heart sound timing interval or the ECG R-wave to ECG R-wave time interval as selected by the system trigger signal 112 for a predetermined number of previous heart detection cycles and compares the average of the previous cycles with the parameter of the present cycle. If the present cycle represents a departure of more than ±25% from the previous average, the data control signal at 408 functions to discard the data in the temporary storage memory 402. In one specific embodiment, four previous heart cycles are averaged.

The temporary storage memory 402 is controlled to accept data in a defined heart cycle in accordance with the input trigger signal at 112. Thus the temporary storage memory 402 accepts data in predetermined data frames for each heart cycle with start and stop data acquisition signals in coincidence with the system trigger signals at 112.

The selected data from the temporary storage memory 402 is output at 412 to a data framing stage 414. After appropriate framing of the data from 412, the data framing stage 414 outputs the appropriately framed data at 416 to an actual analysis memory 418 of diagnostic apparatus. The data framing stage 414 receives a frame control signal at 420 from the portion controller 404.

Specific diagnostic apparatus including the actual memory 418 that is suitable for the analysis in accordance with the present invention is the SCINTIVIEW TM data analysis apparatus available from Siemens Gammasonics, Nuclear Medicine Division.

In operation, the temporary storage memory 402 is controlled by the system trigger signal 112 to acquire data at 400 for each heart cycle after the collection of the data. Assume that the arrhythmia detector 410 determines that the heart cycle is valid for analysis based on the system trigger signals at 112. In accordance with the second heart sound signal at 108 occurring during the heart cycle for which data is obtained, the portion controller 404 determines the data frames within the temporary storage memory 402 that are of interest for analysis. Thus, the portion controller outputs at 406, the address signals that represent the data frames to be output to the data framing stage 414. Further, after the output of data at 412, the temporary storage memory erases the stored data. In this regard the data from two or more heart cycles may be simultaneously stored within the temporary storage memory 402. The portion controller 404 also outputs the control framing signal 420 to condition the data framing stage 414 to appropriately format the output at 412 into a desired number of data frames suitable for use by the diagnostic apparatus. For example, in a specific embodiment, the data framing stage 414 appropriately frames the selected data at 412 into 16 data frames.

Thus, the arrangement of FIG. 8 functions to control the acquisition of data and perform a mid-course cardiac cycle correction for selecting appropriate data for analysis for imaging purposes. Specifically, assume that the temporary storage means 402 is arranged to store data in 10 millisecond frames with a total number of 100 data frames for a particular heart detection cycle. Further, assume that the portion controller 404 receives the second heart signal at 108 coincident with the 33rd data frame time interval. In accordance with the control settings of the portion controller 404, the signal 406 directs the temporary storage memory 402 to read out the 33rd through 67th data frames at 412 while the remaining data is either erased immediately or merely disregarded. The control signal 420 provides a framing interval signal such as to define 16 data frames of approximately 20 millisecond data frame intervals. Of course, it should be understood that a different range of data frames such as the 25th to 60th frames or any other range may be selected for analysis relative to teh systole trigger signal 108 with any desired data frame interval in accordance with the analysis purposes.

It should be understood that the arrhythmia detector 410 and the portion controller 404 in specific embodiments are capable of independent operation relative to each other in the control of the temporary storage memory 402.

Considering other specific arrangements for the control of diagnostic apparatus by the present invention, the second heart sound signal either at 108 or as selected by the system trigger selector 110 at 112 (FIG. 4a) is utilized to directly control the acquisition of data by diagnostic apparatus to accurately acquire data for analysis for gated blood pool studies or the like.

Prior detection and gating techniques utilizing the ECG R-wave delay triggering are extremely susceptible to problems during stress test studies. As the heart cycle changes rapidly, the programmed delay will no longer approximatley gate the analysis data at systole. Some prior systems have attempted to ignore heart cycle data by averaging techniques such as by rejecting all heart cycle data when the R-R wave signal rate varies by more than a predetermined amount. Such arrangements are unable to properly evaluate and accept data due to the rapidly changing heart rate. In the case where arrhythmia is present, effective data analysis and triggering becomes extremely complex and nearly impossible.

This mode of operation utilizing an accurately timed systolic heart sound is especially useful in analyzing the cardiac function of patients undergoing stress studies wherein noise on the heart sound signal input is at increased levels rendering prior known heart sound detection and gating techniques extremely inaccurate and unreliable. Thus, accurate systolic gating or analysis utilizing the systolic heart sound trigger as a reference point in extremely valuable to achieve meaningful analytical results.

The control of diagnostic apparatus with the use of the present invention is also extremely useful for analysis by gating an image or data analysis with the diastolic (first heart sound trigger signal) and by gating an image or data analysis with the systolic (second) heart sound trigger signal for an accurate and simple assessment of left ventricular ejection fraction and heart wall motion. Further, the systole (second) heart sound trigger signal can be utilized to trigger multiple gated images to start a study at the systole point of the cardiac cycle and to evaluate the rate and quality of left ventricular filling phase.

While there has been illustrated and described various embodiments of the present invention, it will be apparent that various changes and modifications thereof will occur to those skilled in the art. For example, the display and control file stage 84 and the digital integrator stage 80 in an alternate embodiment are arranged to operate step by step in a predetermined manner throughout the fifteen ranges of operation. For example, the display control file 84 in another alternate embodiment is arranged to step through the 15 values of operation starting from value 15 one step at a time to range one until proper detection is achieved. Further the display and control file stage 84 in combination with other stages of the apparatus 10 in another alternate embodiment are configured by a microprocessor to supply a continuously variable time window control signal to the digital filter 74 and the digitally variable time window stage 90 in accordance with the depiction of FIG. 7. Further, the ranges of operation are merely illustrative and can of course be chosen as desired.

Accordingly, it is intended in the appended claims to cover all such changes and modifications as fall within the true spirit and scope of the present invention.

What is claimed as new and desired to be secured by Letters Patent of the United States is:

1. A method of controlling diagnostic apparatus to acquire cardiac or heart function data or images comprising the steps of:
   detecting the occurence of a first heart sound and a second heart sound when both are coincident with a prescribed heart sound enable window adjustable within prescribed limits and beginning with the occurence of the first heart sound;
   providing an accurately timed systole trigger signal coincident with systole heart function as derived from the heart sound signal; and
   controlling data acqustion of diagnostic apparatus in accordance with said accurately time systole trigger signal.

2. The method of claim 1 further comprising the steps of providing an accurately timed diastole trigger signal coincident with diastole heart function as derived from the heart sound signal; and
   controlling data acquisition of the diagnostic apparatus in accordance with said accurately timed diastole trigger signal.

3. The method of claim 2 wherein said diastole and systole controlling steps further comprise the steps of gating a diastolic image in accordance with said diastolic trigger signal and gating a systolic image in accordance with said systolic trigger signal.

4. The method of claim 1 wherein said controlling step comprises the step of obtaining multiple data frames by starting data acquisition at systole and obtaining data at a predetermined number of points thereafter.

5. A method of controlling diagnostic apparatus of the type which produces cardiac cycle analysis data comprising:
   storing cardiac cycle analysis data for a cardiac cycle in a temporary storage memory, the cardiac cycle analysis data being stored in serial time relationship;
   detecting the occurrence of a first occuring heart sound;
   detecting the occurrence of a second occuring heart sound within a pre-established heart sound enable window adjustable between prescribed limits until the detection of the second heart sound;
   producing an accurately timed heart sound signal in accordance with the second occuring heart sound signal;
   selecting a portion of the temporarily stored data that is desired for data analysis in accordance with the accurately timed heart sound signal; and
   controlling the read-out of the desired portion of the temporarily stored data for data analysis to diagnostic apparatus.

6. The method of claim 5 further comprising the steps of:
   determining the cardiac rate of the present cardiac cycle data;
   detecting whether or not the present cardiac cycle data represents a departure of the cardiac rate by a predetermined amount from the average of a predetermined number of previous cardiac cycles based on either the heart sound rate, and inhibiting the read-out of the temporarily stored data to the diagnostic apparatus in accordance with said detecting step.

7. The method as in either claim 5 or claim 6 wherein said controlling step further comprises framing the read-out data to the diagnostic apparatus with a predetermined number of data frame time intervals.

8. The method of claim 7, further comprising the steps of:
   producing an accurately timed diastole heart sound in accordance with the first occuring heart sound; and
   starting the providing of data to the temporary storage memory in accordance with an accurately timed diastole heart sound.

9. The method of claim 7 further comprising the steps of:
   detecting an EGC wave signal;
   producing an ECG-R wave signal in predetermined relationship to the detected EGC wave signal; and
   starting the providing of data to the temporary storage memory in accordance with the ECG-R wave signal.

10. The method of claim 8 wherein said starting step further comprises the step of controlling the addressing of the temporary storage memory upon the occurence of each data starting step to store the data from each successive cardiac cycle in predetermined different locations defining independent cardiac cycle data.

11. Apparatus for controlling the acquiring and reading-out of cardiac cycle data produced by diagnostic apparatus, the cardiac cycle data being produced in association with an ongoing heart sound signal comprising:
    first means for temporarily storing cardiac cycle data, said cardiac cycle data being received at a data input and representing one or more cardiac parameters in serial time relationship;
    second means responsive to the ongoing heart sound signal for producing a trigger signal in predetermined time relationship to the ongoing heart sound signal to select the portion of said stored cardiac cycle data that is desired for data analysis by additional diagnostic apparatus; and
    means responsive to said second means for controlling the read-out of said desired portion data from said temporary storing means.

12. The apparatus of claim 11 further comprising arrythmia detector means for detecting cardiac cycle data in said temporary storage means corresponding to a cardiac cycle that represents a cardiac rate that is a departure from previous cardiac cycles by a predetermined amount, said readout controlling means being responsive to said arrythmia detector means and further comprising means for inhibiting the read-out of detected arrythmia cardiac cycle data and discarding said detected arrythmia cardiac cycle data in said temporary storage means.

13. The apparatus of claim 12 further comprising data framing means for formulating said read-out data into a predetermined number of data frame time intervals.

14. The apparatus of claim 11 further comprising means for generating an accurately timed systole heart sound signal connected to said second means.

15. The apparatus of claim 14 wherein said second means comprises means for selecting said data portion in accordance with a predetermined relationship defining the desired portion of the cardiac cycle with respect to the occurrence of systole, said second means further means for selecting a cardiac reference signal from a plurality of signals including a diastole heart sound signal and an ECG-R wave signal.

* * * * *